(12) United States Patent
Miyasa et al.

(10) Patent No.: US 10,682,060 B2
(45) Date of Patent: Jun. 16, 2020

(54) PHOTOACOUSTIC APPARATUS AND IMAGE PROCESSING METHOD

(71) Applicant: CANON KABUSHIKI KAISHA, Tokyo (JP)

(72) Inventors: Kazuhiro Miyasa, Yokohama (JP); Ryo Ishikawa, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 991 days.

(21) Appl. No.: 15/080,779

(22) Filed: Mar. 25, 2016

(65) Prior Publication Data

US 2016/0296120 A1 Oct. 13, 2016

(30) Foreign Application Priority Data

Apr. 10, 2015 (JP) .................. 2015-080675

(51) Int. Cl.
*A61B 5/00* (2006.01)
*A61B 5/1455* (2006.01)
*A61B 5/11* (2006.01)

(52) U.S. Cl.
CPC .......... *A61B 5/0095* (2013.01); *A61B 5/0035* (2013.01); *A61B 5/7207* (2013.01); *A61B 5/1128* (2013.01); *A61B 5/14551* (2013.01)

(58) Field of Classification Search
CPC . A61B 5/0095; A61B 5/7207; A61B 5/14551; A61B 5/1128; A61B 5/0035
See application file for complete search history.

(56) References Cited

U.S. PATENT DOCUMENTS

| 8,345,927 | B2 | 1/2013 | Ishikawa et al. ............. 382/106 |
| 9,123,096 | B2 | 9/2015 | Miyasa et al. ........ G06T 7/0012 |
| 2010/0049044 | A1 | 2/2010 | Burcher ........................ 600/437 |
| 2011/0262015 | A1 | 10/2011 | Ishikawa et al. ............. 382/128 |
| 2012/0262460 | A1 | 10/2012 | Endo et al. ................... 345/441 |
| 2014/0023254 | A1 | 1/2014 | Ishikawa et al. ............. 382/131 |

*Primary Examiner* — Boniface N Nganga
(74) *Attorney, Agent, or Firm* — Venable LLP

(57) ABSTRACT

A photoacoustic apparatus is used which includes: a receiving element receiving acoustic wave from an object; a processor generating image data inside of the object; a changer changing irradiation positions of light on the object; and a wide-area image acquirer of the object, wherein the processor generates, for the irradiation positions, a local-area image of the object corresponding to the irradiation position, and based on a comparison between a plurality of local-area images obtained for the irradiation positions and a comparison between the plurality of local-area images and the wide-area image, integrates the plurality of local-area images.

14 Claims, 15 Drawing Sheets

PHOTOACOUSTIC APPARATUS AND IMAGE PROCESSING METHOD

BACKGROUND OF THE INVENTION

Field of the Invention

The present invention relates to a photoacoustic apparatus and an image processing method.

Description of the Related Art

One imaging technique for visualizing the inside of an object is photoacoustic imaging. With photoacoustic imaging, first, an object is irradiated with pulsed light generated from a light source. As the irradiation light is propagated and diffused inside the object and absorbed by a light absorber such as hemoglobin in blood, an acoustic wave (a photoacoustic wave) is generated due to a photoacoustic effect. A plurality of receiving elements arranged around the object receives the photoacoustic wave and outputs a reception signal (a photoacoustic signal). By having a processor analyze the photoacoustic signal and perform image reconstruction, image data (a photoacoustic image) representing an optical characteristic value regarding the inside of the object is obtained.

Due to many factors, a photoacoustic signal may contain noise that causes a decline in SN ratio. Performing image reconstruction using a signal with low SN ratio results in low quantitativity of optical characteristic information. US Patent Application Publication No. 2010/0049044 discloses a method of reducing noise by performing pulsed light irradiation and photoacoustic signal measurement a plurality of times and averaging the plurality of acquired photoacoustic signals. Furthermore, US Patent Application Publication No. 2010/0049044 discloses a method of acquiring an ultrasonic image whose position is associated with that of a photoacoustic image and tracking the ultrasonic image to estimate and correct a body motion of an object. Moreover, photoacoustic signals after body motion correction are averaged to produce a greater noise reduction effect.

When an object is irradiated with pulsed light, there is a limit to a range in which imaging can be performed with high quality based on photoacoustic signals. This range is referred to as a field of view (FOV). Therefore, when an imaging object region of an object is greater than a FOV, photoacoustic signals are obtained by moving an irradiation position of pulsed light and shifting the FOV in small increments. In addition, by averaging the respective photoacoustic signals in consideration of the amount of movement, imaging can be performed with high precision on a wide imaging object region. When the body motion estimation described in US Patent Application Publication No. 2010/0049044 is to be performed on data captured by moving an irradiation position in this manner, correction of positional displacement is time-sequentially performed for each adjacent FOV of the object.

Patent Literature 1: US Patent Application Publication No. 2010/0049044

SUMMARY OF THE INVENTION

However, with the method described above, a photoacoustic image after averaging may end up being distorted with respect to an original anatomical structure of the object due to an accumulation of errors in local correction.

The present invention has been made in consideration of the problems described above. An object of the present invention is to provide a method of generating a high-quality photoacoustic image even when an object moves during photoacoustic imaging or the like.

The present invention provides a photoacoustic apparatus comprising:

a light source;

a receiving element configured to receive an acoustic wave generated from an object irradiated with light from the light source;

a processor configured to generate image data representing characteristics information regarding the inside of the object using the acoustic wave;

a changer configured to change irradiation positions of the light on the object; and a wide-area image acquirer configured to acquire a wide-area image of the object, wherein the processor is configured to:

generate, for the irradiation positions that are changed by the changer, a local-area image that is the image data in a local area of the object corresponding to the irradiation position, and based on a first comparison that is a comparison between a plurality of local-area images obtained for the irradiation positions and a second comparison that is a comparison between the plurality of local-area images and the wide-area image, integrate the plurality of local-area images.

The present invention also provides an image processing method for generating image data representing characteristics information regarding the inside of an object irradiated with light while changing irradiation positions using an acoustic wave generated from the object, the image processing method comprising:

acquiring a wide-area image of the object;

generating, for the changing irradiation positions, a local-area image that is the image data in a local area of the object corresponding to the irradiation position; and based on a comparison between a plurality of the local-area images obtained for the irradiation positions and a comparison between the plurality of local-area images and the wide-area image, integrating the plurality of local-area images.

According to the present invention, a method of generating a high-quality photoacoustic image even when an object moves during photoacoustic imaging or the like can be provided.

Further features of the present invention will become apparent from the following description of exemplary embodiments with reference to the attached drawings.

DESCRIPTION OF THE EMBODIMENTS

Figure 1:
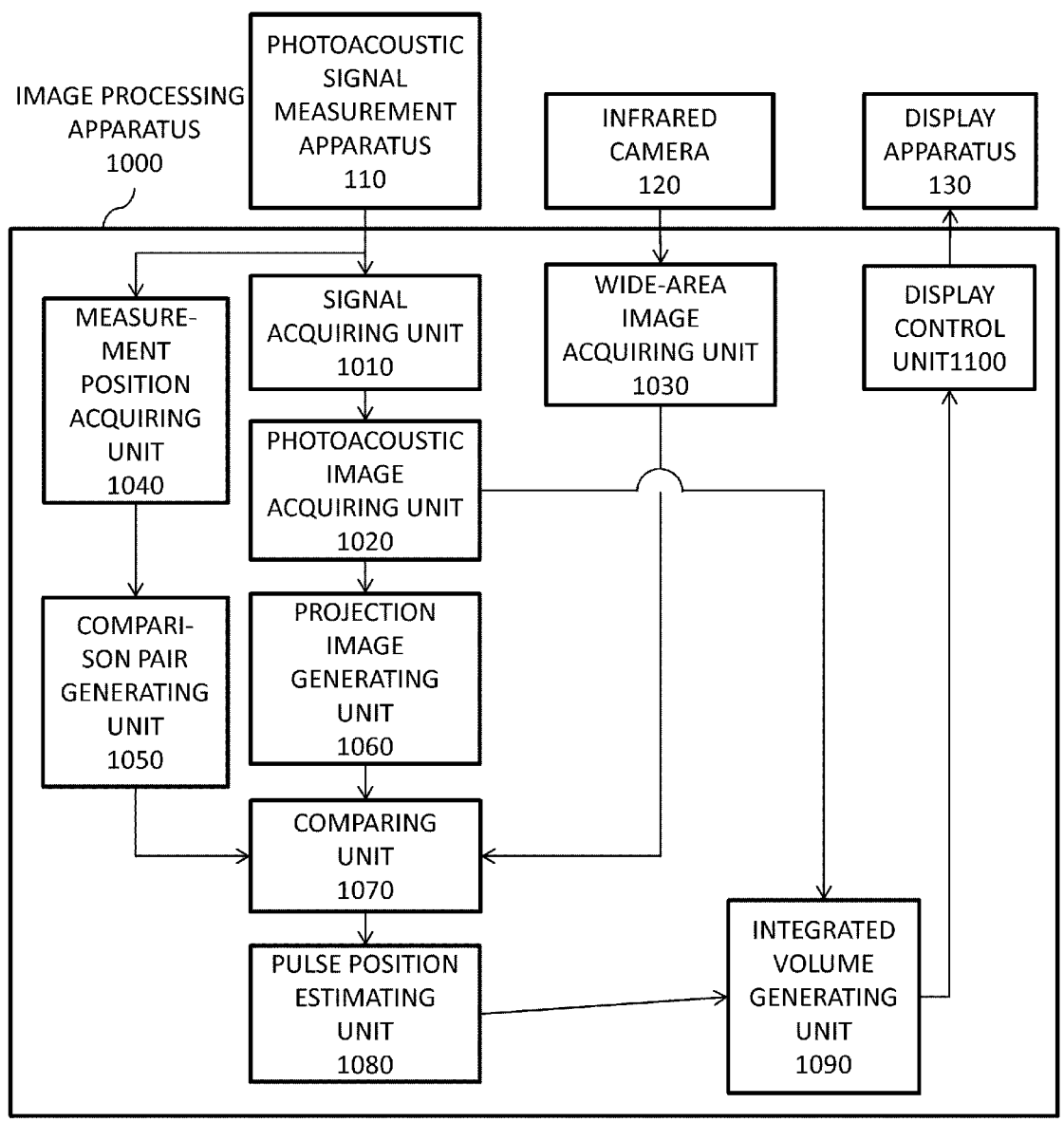
FIG. 1 is a diagram showing a functional configuration of an image processing apparatus according to a first embodiment.

Hereinafter, preferred embodiments of the present invention will be described with reference to the drawings. However, it is to be understood that dimensions, materials, shapes, relative arrangements, and the like of components described below are intended to be changed as deemed appropriate in accordance with configurations and various conditions of apparatuses to which the present invention is to be applied. Therefore, the scope of the present invention is not intended to be limited to the embodiments described below.

The present invention relates to a technique for detecting an acoustic wave propagating from an object and generating and acquiring characteristics information regarding the inside of the object. Accordingly, the present invention can be considered an object information acquiring apparatus or a control method thereof, or an object information acquiring method and a signal processing method. The present invention can also be considered a program that causes an information processing apparatus including hardware resources such as a CPU to execute these methods or a storage medium storing the program. The present invention can also be considered an apparatus which corrects characteristics information regarding the inside of an object or a control method thereof, a characteristics information correction method, or a characteristics information correction program. Since the present invention also provides a function for processing image data representing characteristics information regarding the inside of an object, the present invention can also be considered an image processing apparatus, an image processing method, and an image processing program.

The object information acquiring apparatus according to the present invention includes an apparatus using photoacoustic tomography technology which irradiates an object with light (an electromagnetic wave) and which receives (detects) an acoustic wave generated at and propagated from a specific position inside the object or on a surface of the object according to a photoacoustic effect. Since such an object information acquiring apparatus obtains characteristics information regarding the inside of an object in a format such as image data based on photoacoustic measurement, the object information acquiring apparatus can also be referred to as a photoacoustic apparatus or a photoacoustic imaging apparatus.

Characteristics information in a photoacoustic apparatus indicates a distribution of generation sources of acoustic waves created as a result of light irradiation, a distribution of initial sound pressure inside an object, a distribution of optical energy absorption density or a distribution of absorption coefficients derived from a distribution of initial sound pressure, or a distribution of concentrations of substances constituting tissue. Specific examples of characteristics information include distribution of oxygenated/reduced hemoglobin concentration, a blood component distribution such as a distribution of oxygen saturation derived from the distribution of oxygenated/reduced hemoglobin concentration, and a distribution of fat, collagen, and water. In addition, characteristics information may be obtained as distribution information of respective positions inside the object instead of as numerical data. In other words, distribution information such as a distribution of absorption coefficients and a distribution of oxygen saturation can be adopted as object information. An image representation of these pieces of distribution information can also be referred to as a photoacoustic image. A photoacoustic image is typically acquired in the form of volume data in which each of three-dimensionally arranged voxels contains a value at a position thereof as distribution information in a three-dimensional space. Volume data can also be referred to as a three-dimensional volume, a three-dimensional image, or a three-dimensional tomographic image.

An acoustic wave according to the present invention is typically an ultrasonic and includes elastic waves that is also referred to as a sonic wave or an acoustic wave. An acoustic wave generated due to a photoacoustic effect is referred to as a photoacoustic wave or an optical ultrasonic wave. An electric signal converted from an acoustic wave by a probe or the like is also referred to as an acoustic signal. An acoustic signal derived from a photoacoustic wave is also referred to as a photoacoustic signal.

First Embodiment

A photoacoustic apparatus according to the present embodiment generates an image that integrates a series of photoacoustic signals measured over a plurality of times. The photoacoustic apparatus estimates a motion such as a body motion of an object which occurs during measurement and corrects a signal so as to reduce the effect of the motion. More specifically, the photoacoustic apparatus compares a plurality of photoacoustic images (local-area images) representing different FOVs with each other and, at the same time, compares each photoacoustic image (local-area image) with an infrared camera image (wide-area image) capturing the entire object. Due to motion estimation using these comparison results, an acoustic image in which distortion is suppressed as a whole with respect to an intrinsic anatomical structure of the object can be obtained.

(Apparatus Configuration)

FIG. 1 shows a configuration of a photoacoustic apparatus according to the present embodiment. As shown in FIG. 1, the photoacoustic apparatus according to the present embodiment includes an image processing apparatus 1000, a photoacoustic signal measurement apparatus 110, an infrared camera 120, and a display apparatus 130. The image processing apparatus 1000 is connected to the photoacoustic signal measurement apparatus 110, the infrared camera 120, and the display apparatus 130.

The photoacoustic signal measurement apparatus 110 irradiates an object with pulsed light, receives a photoacoustic wave generated due to a photoacoustic effect with a plurality of receiving elements around the object, and converts the received photoacoustic waves into an electric signal (photoacoustic signal). The photoacoustic signal measurement apparatus 110 repetitively performs pulsed light irradiation and photoacoustic signal measurement a plurality of times. If it is assumed that one set of photoacoustic signals corresponds to one pulsed light irradiation (or one FOV), sets of photoacoustic signals corresponding to the number of pulsed light irradiations are to be acquired. The measured photoacoustic signals are input to the image processing apparatus 1000.

(FOV)

Figure 2:
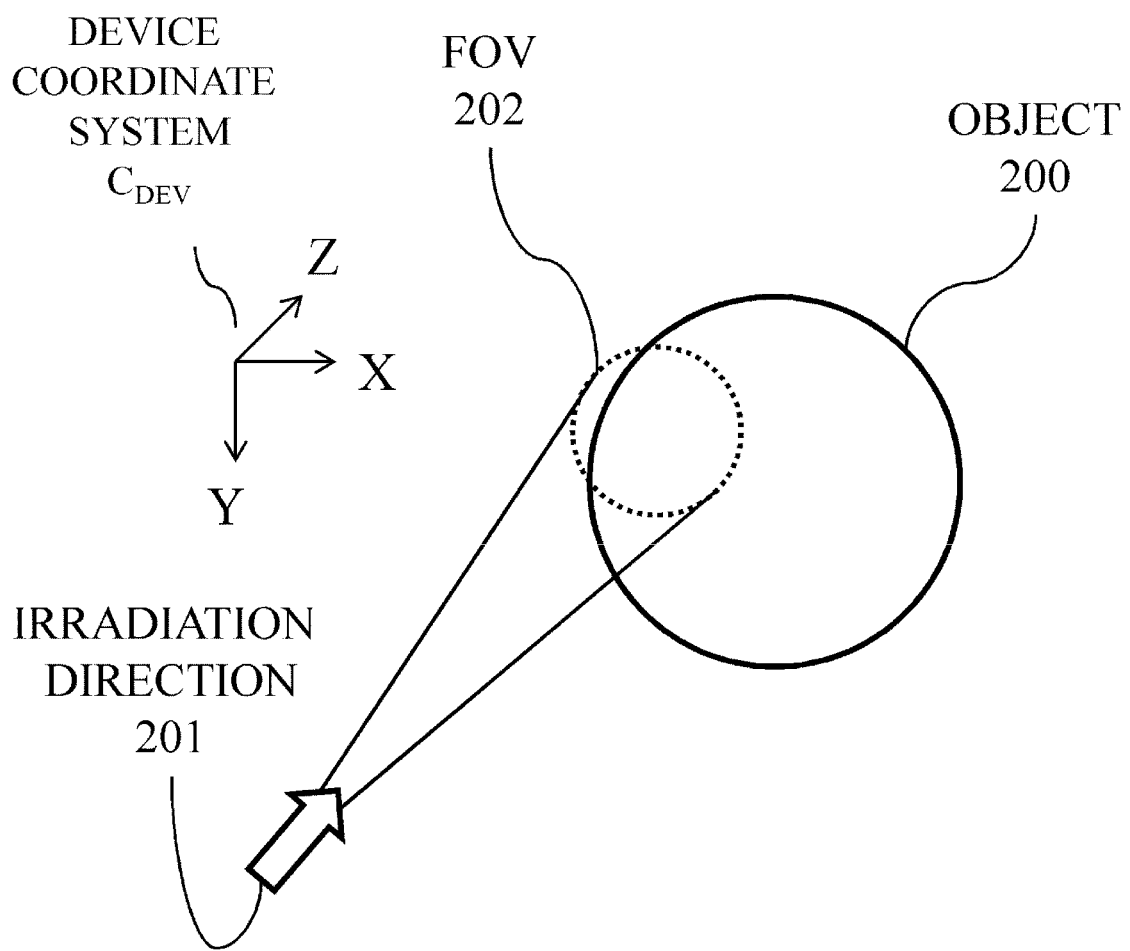
FIG. 2 is a diagram showing a range in which imaging of an object can be performed by a photoacoustic signal measurement apparatus.

FIG. 2 shows a range (FOV) in which imaging of an object can be performed by a photoacoustic signal measurement apparatus. A FOV 202 is a range where imaging can be performed when an object 200 is irradiated with pulsed light in a irradiation direction 201. The irradiation direction 201 according to the present embodiment is parallel to a Z axis of a device coordinate system $C_{DEV}$ of the photoacoustic signal measurement apparatus 110. As shown in FIG. 2, when the entire object 200 cannot be covered by one FOV, photoacoustic signals must be acquired from the entire object by shifting the FOV in small increments for each light irradiation. This can be accomplished by methods such as configuring an emitting end of light to be movable and configuring the light irradiation direction to be changeable. Such configurations enable cases where a region of interest is larger than one FOV to be accommodated. Moreover, a FOV position is favorably recorded for each pulse irradiation to be used in subsequent image integration. Examples of a position recording method include a method of recording a reference coordinate that represents a light irradiation position or the like.

(Photoacoustic Signal Measurement Apparatus)

FIG. 15 shows a configuration example of the photoacoustic signal measurement apparatus 110. An object 1500 that is a measurement object is, for example, a breast of a living body. The photoacoustic signal measurement apparatus 110 communicates with the image processing apparatus 1000 to receive control information and transmit acquisition signals. The photoacoustic signal measurement apparatus may be considered corresponding to the photoacoustic apparatus according to the present invention or a combination of the photoacoustic signal measurement apparatus and the image processing apparatus may be considered the photoacoustic apparatus.

Figure 15A:
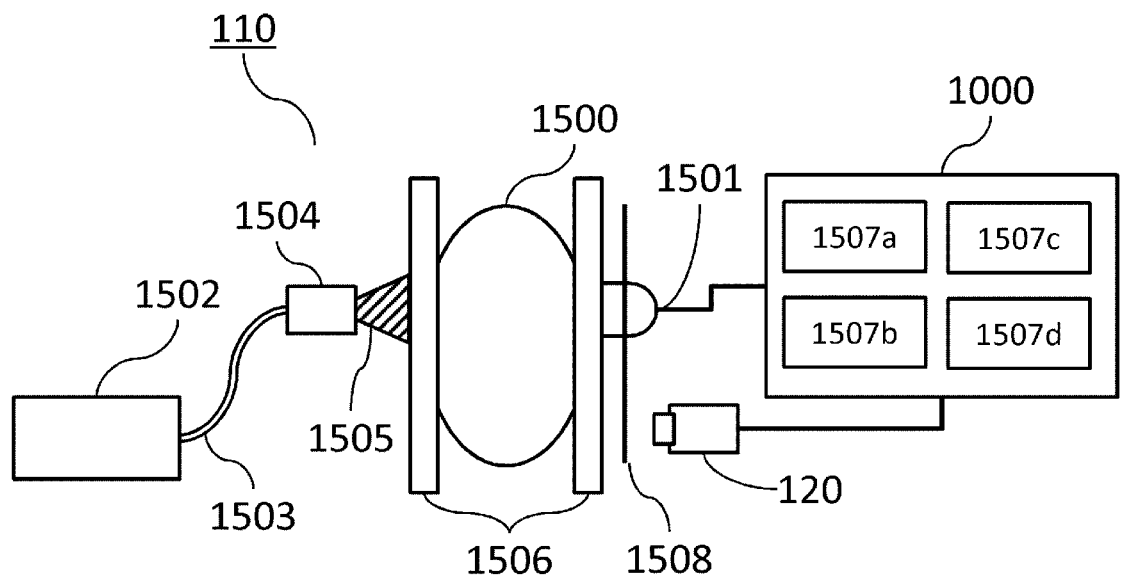
FIGS. 15A and 15B are diagrams showing a configuration example of a photoacoustic signal measurement apparatus.

FIG. 15A shows an apparatus which sandwiches the object 1500 with two plate-like holding members 1506. Pulse light 1505 generated from a light source 1502 is transmitted by an optical system 1503 and irradiates the object from an emitting end 1504. A plurality of receiving elements 1509 (a to n) arranged on a probe 1501 detect photoacoustic waves generated from the object and converts the photoacoustic waves into photoacoustic signals that are analog electric signals, and transmit the analog electric signals to the image processing apparatus 1000. The receiving elements can also be referred to as signal measuring units that measure photoacoustic signals.

Figure 15B:
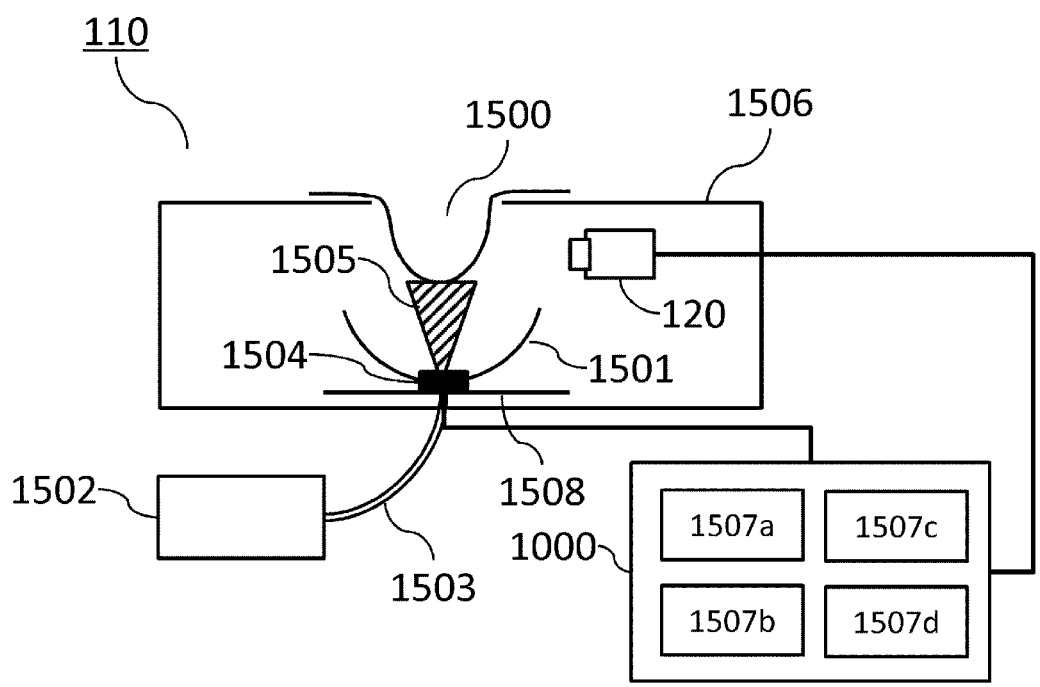

On the other hand, FIG. 15B shows an apparatus which suspends the object 1500 from an opening of a box-like holding member 1506. In FIG. 15B, a plurality of receiving elements arranged on a bowl-like probe 1501 measure photoacoustic waves. In this mode, a high resolution region is formed where high sensitivity directions of the receiving elements concentrate. In this case, the probe and the receiving elements correspond to the signal measuring unit. Favorably, a cup-like supporting member that transmits light and acoustic waves is also provided in order to support the object and stabilize the shape thereof.

While the image processing apparatus 1000 has been described from the perspective of functional blocks with reference to FIG. 1, the image processing apparatus 1000 will now be described from the perspective of a physical configuration with reference to FIG. 15. For example, the image processing apparatus 1000 is configured to include a CPU 1507a, a GPU 1507b, a memory 1507c, and an FPGA 1507d. An image processing method is realized as the respective blocks perform information processing and signal processing. Alternatively, information processing may be performed using online computing resources.

A laser light source capable of generating pulse laser light is favorable as the light source 1502. Alternatively, a flash lamp or an LED light source can be used. Optical members such as bundle fiber, a prism, a mirror, and a lens are preferable as the optical system. 1503 and the emitting end 1504. As the receiving elements provided on the probe 1501, for example, piezoelectric elements, capacitance type elements, and Fabry-Perot elements can be used. A signal processing circuit that performs an amplification process and a digital conversion process on photoacoustic signals is favorably provided between the probe and the image processing apparatus or inside the image processing apparatus.

By providing a changer 1508 which moves the emitting end 1504 and changes light irradiation positions and changing relative positions of the object 1500 and the emitting end, the position of the FOV is moved in small increments and the entire object is measured. The changer may move the probe together with the emitting end. For example, a drive part such as a motor or a control stage is preferable as the changer. The changer may move the object instead. Alternatively, the changer may change the light irradiation position and, in turn, the FOV by changing light irradiation directions.

(Infrared Camera)

The infrared camera 120 photographs an external appearance of an object and a blood vessel near a body surface of the object as a still image or a moving image and inputs the photographed image to the image processing apparatus 1000. The infrared camera 120 is installed at a position that enables the external appearance of the entire object to be photographed. In the present embodiment, three infrared cameras are used. When the three infrared cameras must be distinguished from one another, the infrared cameras will be respectively denoted by reference numerals 301, 302, and 303.

Figure 3:
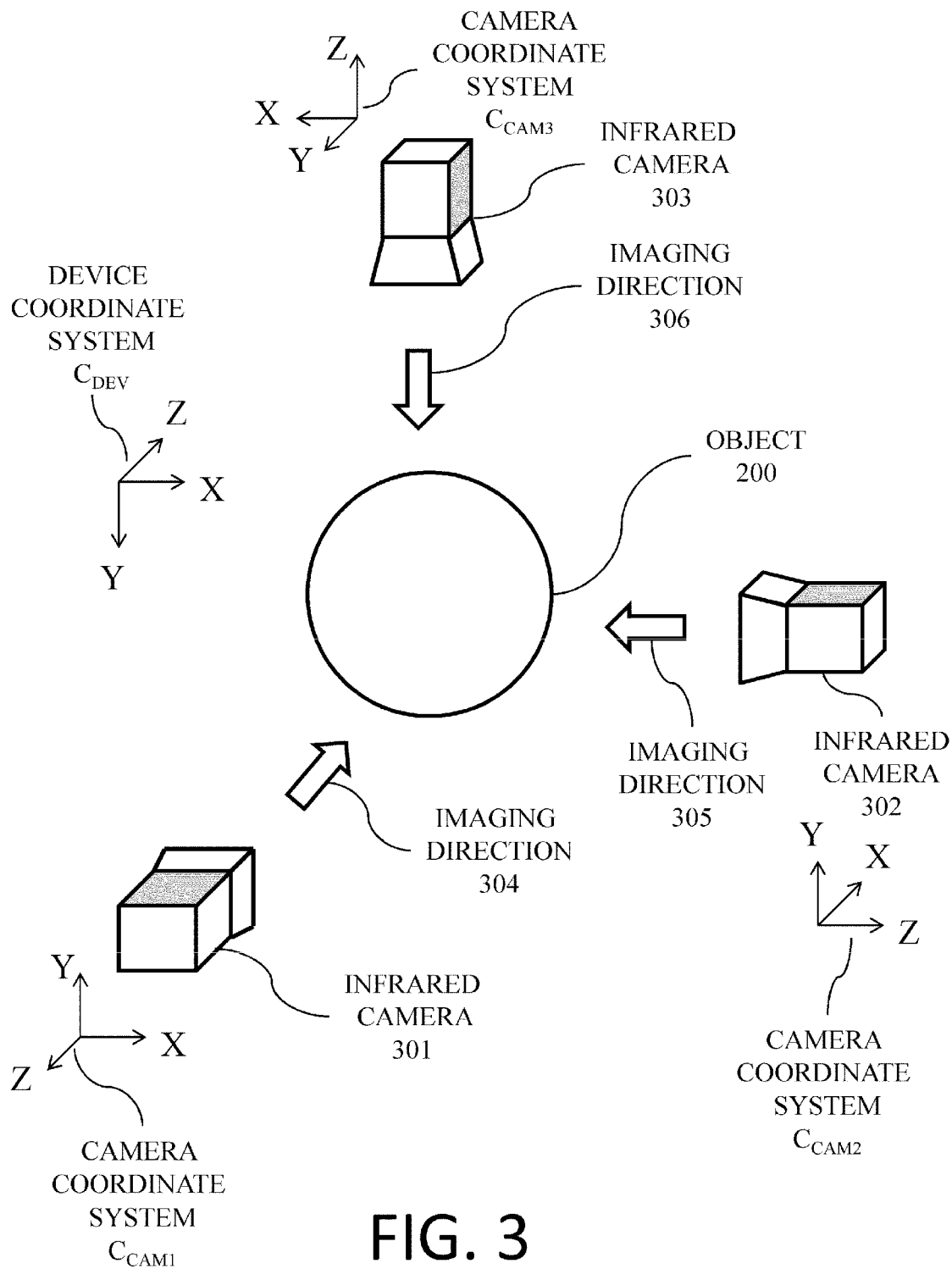
FIG. 3 is a diagram showing imaging of an object being performed by infrared cameras.

FIG. 3 shows imaging performed by infrared cameras. An imaging direction 304 of the infrared camera 301 is consistent with the Z direction of the device coordinate system $C_{DEV}$ (in other words, a Z axis of a camera coordinate system $C_{CAM1}$ is oriented in a −Z direction of the device coordinate system $C_{DEV}$). An imaging direction 305 of the infrared camera 302 is consistent with a −X direction of the device coordinate system $C_{DEV}$ (in other words, a Z axis of a camera coordinate system $C_{CAM2}$ is oriented in an X direction of the device coordinate system $C_{DEV}$). An imaging direction 306 of the infrared camera 303 is consistent with a Y direction of the device coordinate system $C_{DEV}$ (in other words, a Z axis of a camera coordinate system $C_{CAM3}$ is oriented in a −Y direction of the device coordinate system $C_{DEV}$). Coordinate transformations from the camera coordinate systems $C_{CAM1}$, $C_{CAM2}$, and $C_{CAM3}$ to the device coordinate system $C_{DEV}$ will be respectively defined as $T_{C1toD}$, $T_{C2toD}$, and $T_{C3toD}$. Each camera has already been calibrated with respect to the device coordinate system $C_{DEV}$ and information regarding the coordinate transformations described above as well as internal parameters of the respective cameras are stored in advance in the image processing apparatus 1000.

Figure 4:
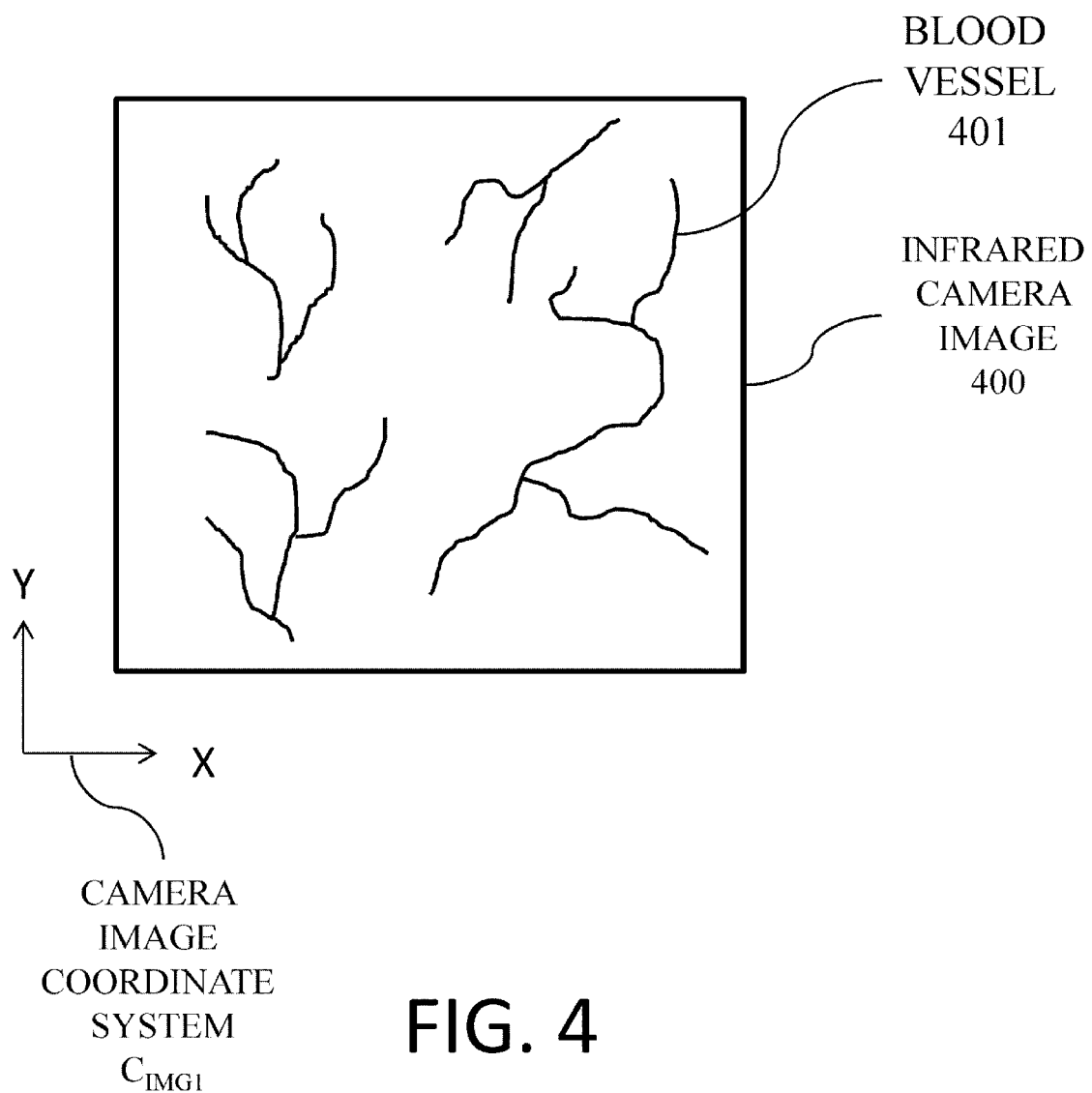
FIG. 4 is a diagram showing an example of an infrared camera image taken by an infrared camera.

FIG. 4 shows an example of an infrared camera image 400 (also referred to as an infrared image) which portrays a blood vessel 401. The infrared cameras are capable of creating an image representation of intensity information of near infrared light. Near infrared light has a characteristic of penetrating skin to a certain degree and a characteristic of being absorbed by a blood vessel portion containing hemoglobin. Therefore, a subcutaneous venous blood vessel (a superficial blood vessel) can be visualized by using an infrared camera. In addition, a blood vessel portion is portrayed darker than its surroundings. Therefore, an infrared camera image can be treated as a morphologic image that clearly depicts a profile of a subcutaneous superficial blood vessel.

Hereinafter, photographed images of the infrared cameras 301, 302, and 303 will be respectively denoted as $I_{CAM1}$, $I_{CAM2}$, and $I_{CAM3}$. Coordinate systems (two-dimensional) of the camera images $I_{CAM1}$, $I_{CAM2}$, and $I_{CAM3}$ will be respectively denoted as $C_{IMG1}$, $C_{IMG2}$, and $C_{IMG3}$. For example, regarding the infrared camera 301, a coordinate on the camera image coordinate system $C_{IMG1}$ (two-dimensional) has a one-to-one relationship with a line of sight of the camera (a straight line that passes through an origin and a point on a projected plane in a three-dimensional space) in the camera coordinate system $C_{CAM1}$ (three-dimensional). A general coordinate transformation method can be used for such transformations between the camera image coordinate system and the camera coordinate system described above. Transformations from the camera coordinate systems $C_{CAM1}$, $C_{CAM2}$, and $C_{CAM3}$ to the camera image coordinate systems $C_{IMG1}$, $C_{IMG2}$, and $C_{IMG3}$ will be respectively defined as $T_{C1toI1}$, $T_{C2toI2}$, and $T_{C3toI3}$.

(Display Apparatus)

The display apparatus 130 is a display such as a liquid crystal apparatus or a CRT. The display apparatus 130 displays an image of an object based on image data output by the image processing apparatus 1000. The display apparatus may be a part of a system or may exist outside of the system.

(Image Processing Apparatus)

The image processing apparatus 1000 includes a signal acquiring unit 1010, a photoacoustic image acquiring unit 1020, a wide-area image acquiring unit 1030, a measurement position acquiring unit 1040, a comparison pair generating unit 1050, and a projection image generating unit 1060. The apparatus further includes a comparing unit 1070, a pulse position estimating unit 1080, an integrated volume generating unit 1090, and a display control unit 1100. The image processing apparatus includes computing resources such as a CPU and a memory, and is constituted by an information processing apparatus (a PC, a work station, or the like) which performs prescribed information processing in accordance with instructions issued by a program. Blocks of the image processing apparatus may be respectively configured as independent circuits or may be virtually realized as a program module.

The signal acquiring unit 1010 acquires a photoacoustic signal measured by the photoacoustic signal measurement apparatus 110 and outputs the photoacoustic signal to the photoacoustic image acquiring unit 1020.

The photoacoustic image acquiring unit 1020 performs an image reconstruction process based on a photoacoustic signal acquired by one pulsed light irradiation and generates a photoacoustic image of a corresponding FOV in a volume data format. Hereinafter, volume data generated for each pulsed light irradiation will be referred to as a pulse volume. The photoacoustic image acquiring unit 1020 outputs the generated pulse volume as a local-area image to the projection image generating unit 1060 and the integrated volume generating unit 1090.

The wide-area image acquiring unit 1030 acquires the infrared camera image (two-dimensional image) captured by the infrared camera 120 as a wide-area image and outputs the wide-area image to the comparing unit 1070.

The measurement position acquiring unit 1040 acquires positional information (signal measurement position) of a signal measuring unit of the photoacoustic signal measurement apparatus 110 and outputs the positional information to the comparison pair generating unit 1050.

The comparison pair generating unit 1050 generates information on a pair of pulse volumes (comparison pair information) and outputs the information to the comparing unit 1070.

The projection image generating unit 1060 generates a projection image from the volume data and outputs the projection image to the comparing unit 1070.

Based on the comparison pair information, the comparing unit 1070 calculates information regarding a degree of matching of projection images of the pulse volumes constituting the pair as a process of comparing the pulse volumes (first comparison). This information is information regarding a degree of matching between the comparison pair on which the projection images are based and can also be referred to as information regarding a positional displacement between the comparison pair. The comparing unit 1070 also calculates information regarding a degree of matching between the projection images of the respective pulse volumes and the infrared camera image as a process of comparing the respective pulse volumes and the infrared camera image with each other (second comparison). This information is information regarding a degree of matching between respective pulse volumes on which the projection images are based and the infrared camera image and can also be referred to as information regarding positional displacements between the respective pulse volumes and the infrared camera image. The respective pieces of calculated information are output to the pulse position estimating unit 1080.

The pulse position estimating unit 1080 calculates estimation values of positions of the respective pulse volumes (pulse position estimation amounts) based on both the information regarding the degree of matching between the pair and the information regarding the degree of matching between the respective pulse volumes and the infrared camera image as calculated by the comparing unit 1070. The calculated estimation values are output to the integrated volume generating unit 1090. Calculating a pulse position estimation amount is equivalent to calculating a correction amount of a position of a pulse volume with respect to a signal measurement position. When a measurement error of a signal measurement position is negligible, the correction amount represents a body motion of an object during each pulsed light irradiation. On the other hand, when the body motion of the object is negligible, the correction amount is a value representing a measurement error of a signal measurement position.

The integrated volume generating unit 1090 generates an integrated volume that integrates pulse volumes based on the pulse position estimation amounts and outputs the integrated volume to the display control unit 1100.

The display control unit 1100 performs display control for displaying the integrated volume generated by the integrated volume generating unit 1090 on the display apparatus 130.

(Processing Flow)

Figure 5:
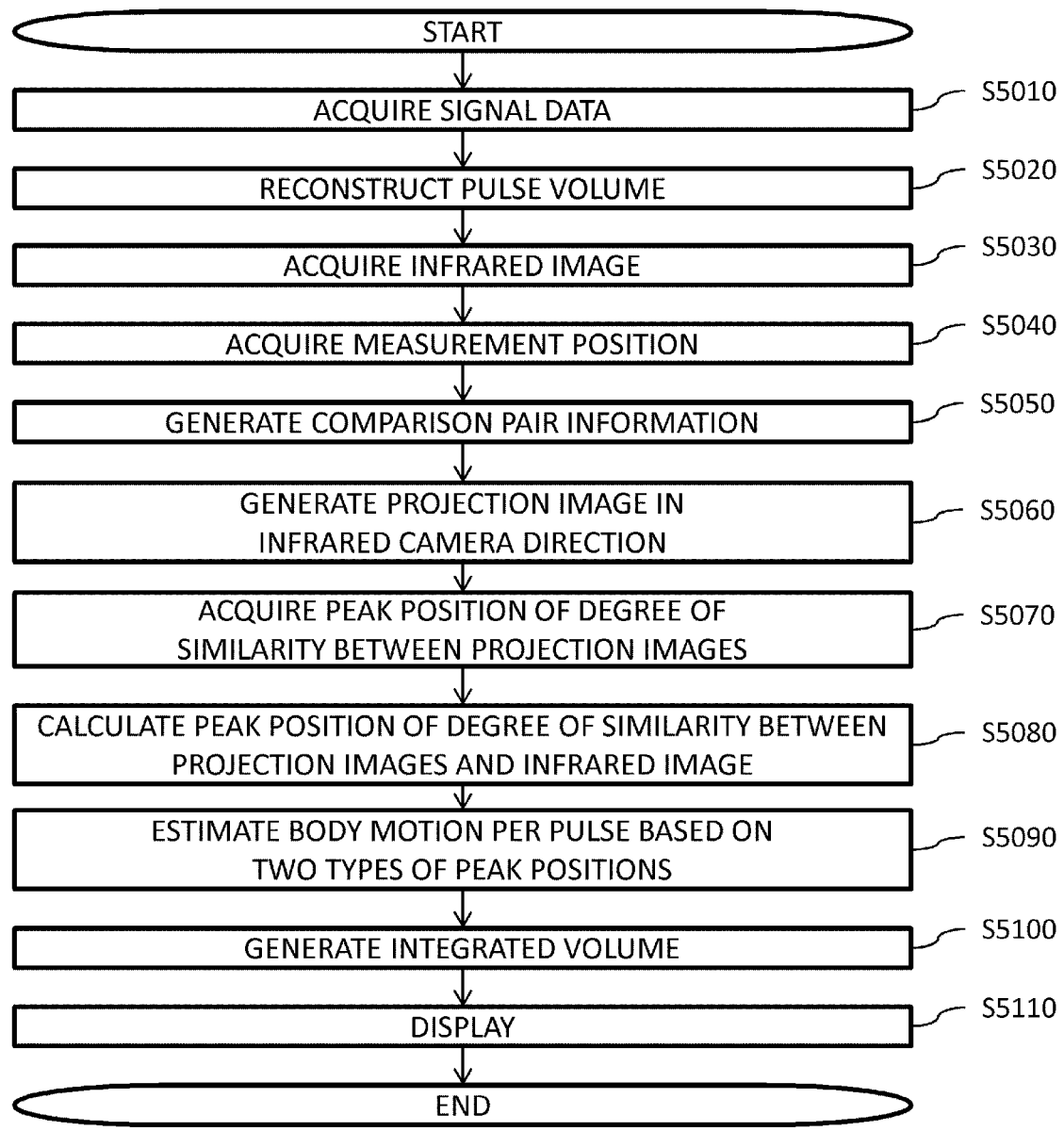
FIG. 5 is a flow chart showing an overall processing procedure according to the first embodiment.

FIG. 5 is a flow chart showing an overall procedure of processing performed by the image processing apparatus 1000.

(Step S5010) Acquisition of Signal Data

The signal acquiring unit 1010 acquires photoacoustic signal data (hereinafter, referred to as signal data) obtained by imaging performed on the object a plurality of times by the photoacoustic signal measurement apparatus 110. In the present embodiment, imaging is performed N_pulse-number of times and N_pulse-number of pieces of signal data are obtained. Signal data received by one (i-th) pulse irradiation will be denoted as P_i ($1 \leq i \leq N\_pulse$). Signal data P_i represents time-sequential acoustic signals received by a plurality of receiving elements when the probe is arranged at a prescribed position. In addition, the index i (where $1 \leq i \leq N\_pulse$ and i is a positive integer) of P_i will be referred to as a "pulse index". Each piece of signal data is expressed in a general form such as a multidimensional data sequence.

(Step S5020) Reconstruction of Pulse Volume

The photoacoustic image acquiring unit 1020 performs a reconstruction process using signal data P_i ($1 \leq i \leq N\_pulse$), generates a pulse volume Vp_i ($1 \leq i \leq N\_pulse$), and records the pulse volume Vp_i ($1 \leq i \leq N\_pulse$) in the image processing apparatus 1000. For the reconstruction, general methods such as a back projection method in a time domain or a Fourier domain which is commonly used in tomographic technology can be used. At this point, a position of each receiving element is taken into consideration. The generated pulse volume Vp_i is image data of a three-dimensional volume and a value of the data (a voxel value) can be expressed by a function expression such as Vp_i (x, y, z). A pulse volume according to the present embodiment is a three-dimensional volume of a local area including a range which enables imaging of the object to be performed (a FOV).

(Step S5030) Acquisition of Infrared Image

The wide-area image acquiring unit 1030 acquires infrared camera images ($I_{CAM1}$, $I_{CAM2}$, and $I_{CAM3}$) of the object photographed by the infrared cameras 301, 302, and 303. In this case, an infrared camera image is assumed to be a still image capturing a given moment. A timing of acquisition of an infrared still image is set within a period of time where a state (a position, a posture, and the like) of the object is unchanged from a point of photoacoustic measurement. Alternatively, an infrared camera may photograph a moving image and the wide-area image acquiring unit 1030 may select a preferable still image from frames of the moving image. In this case, a frame with minimal change to the image is favorably detected by, for example, a method of obtaining differences in pixel values between the frames.

(Step S5040) Acquisition of Measurement Position

The measurement position acquiring unit 1040 acquires a signal measurement position of the photoacoustic signal measurement apparatus 110. A signal measurement position refers to a position of a signal measuring unit at a point of measurement of each of the N_pulse-number of pieces of signal data acquired in step S5010 and is three-dimensional positional information in the device coordinate system $C_{DEV}$. The signal data acquired in step S5010 and the pulse volume generated based on the signal data are measurement results with respect to a prescribed range (FOV) with this signal measurement position as a reference. In the present embodiment, a signal measurement position is expressed as PosS_i ($1 \leq i \leq N\_pulse$). When the signal measuring unit performs photoacoustic measurement while being moved by a position changer, the signal measurement position differs for each pulse.

(Step S5050) Generation of Comparison Pair Information

The comparison pair generating unit 1050 acquires the signal measurement position PosS_i, determines a comparison pair on which a subsequent comparison process is to be performed, and generates comparison pair information. Examples of determination criteria of the pair include a method of adopting pulse volumes that overlap with each other as a pair.

Figure 6:
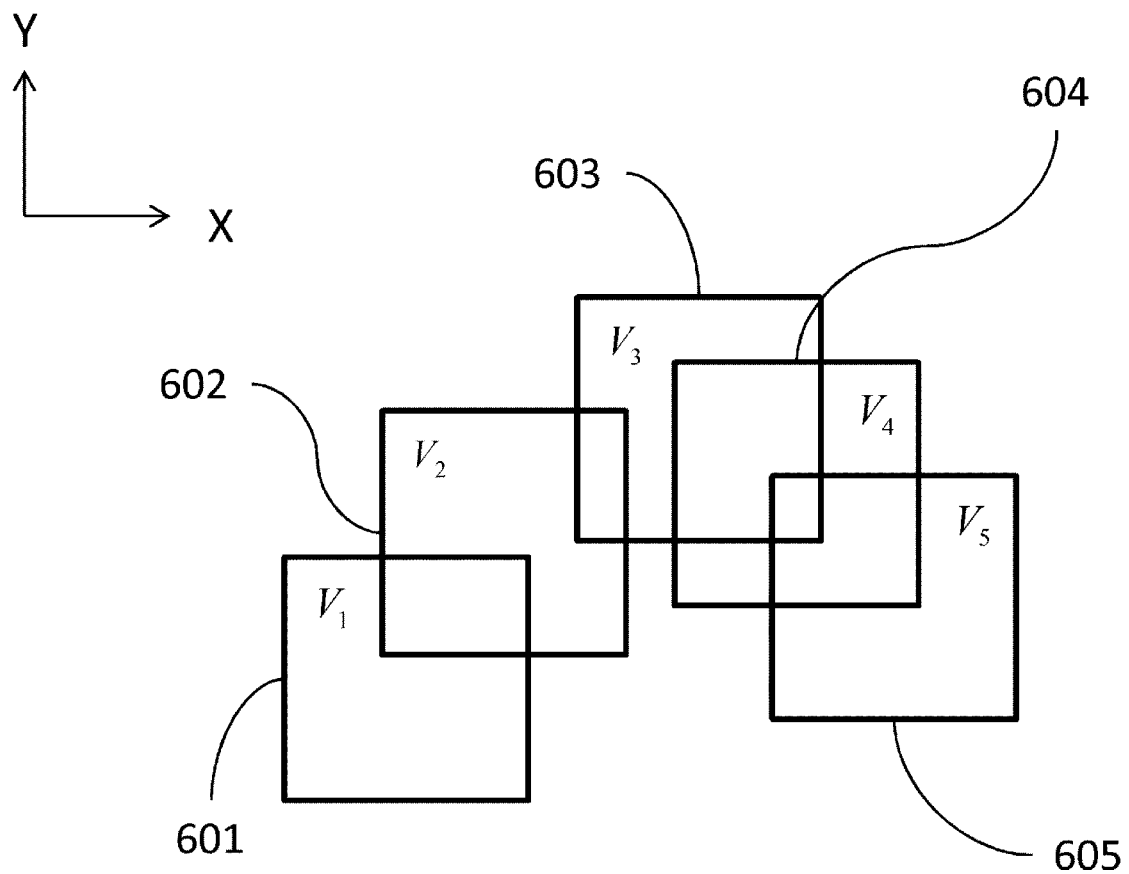
FIG. 6 is a diagram showing a method of generating comparison pair information.

FIG. 6 is a diagram for explaining a method of generating comparison pair information. Due to restrictions imposed by a paper-based description, the description will be simplified into two dimensions. Reference numerals 601 to 605 respectively denote regions of pulse volumes V1 to V5 which correspond to signal measurement positions PosS_i (i=1 to 5). The comparison pair generating unit 1050 detects a pair of pulse volumes having an overlapping region among these pulse volumes. In this case, regions of "V1 and V2", "V2 and V3", "V3 and V4", "V3 and V5", and "V4 and V5" overlap each other. Therefore, the comparison pair generating unit 1050 generates information indicating these pairs as sets of pulse indices. In the case of FIG. 6, R_1={1, 2}, R_2={2, 3}, R_3={3, 4}, R_5={3, 5}, and R_5={4, 5}.

However, a method of generating comparison pair information is not limited to the above. Alternatively, for example, a method may be used in which pulse volumes whose overlapping region has a volume equal to or higher than a prescribed value are adopted as a pair. In addition, a method may be used in which pulse volumes whose overlapping region has a ratio of volume that is equal to or higher than a prescribed value are adopted as a comparison pair. According to these methods, since a pair is not formed if an amount or a ratio of an overlapping region is small, efficiency and stability of an estimation process of positions between pulse volumes are improved.

(Step S5060) Generation of Projection Image in Infrared Camera Direction

In step S5060, the projection image generating unit 1060 projects a volume value and generates a projection image for each of the pulse volumes Vi ($1 \leq i \leq N\_pulse$). For example, a maximum intensity projection (MIP) image is generated. The image can be generated using a general method such as a perspective projection method. A projection direction of the projection image is set approximately the same as (favorably, consistent with) imaging directions (304, 305, and 306) of the respective infrared cameras. In other words, a projection image is generated in each of a Z axis direction, an X axis direction, and a Y axis direction of the device coordinate system $C_{DEV}$. This is because, in step S5080 (to be described later), a projection image (a local-area image) and an infrared camera image (an object wide-area image) are to be compared from a same direction.

A case where a perspective projection method is used will be described in detail. As described earlier, coordinate transformations from the respective camera coordinate systems to the device coordinate system are defined as $T_{C1toD}$, $T_{C2toD}$, and $T_{C3toD}$. In addition, transformations from the respective camera coordinate systems (three-dimensional) to the camera image coordinate system (two-dimensional) are defined as $T_{C1toI1}$, $T_{C2toI2}$, and $T_{C3toI3}$. Therefore, translation corresponding to the signal measurement position PosS_i is imparted to a coordinate of each voxel of a pulse volume for the transformation to the device coordinate system, and an inverse transformation of $T_{C1toD}$, $T_{C2toD}$, and $T_{C3toD}$ are applied to the respective results for the transformation to the infrared camera coordinate system. Subsequently, transformations of $I_{C1toI1}$, $T_{C2toI2}$, and $T_{C3toI3}$ are respectively further applied to the results for the transformation to the infrared camera image coordinate system. In other words, a calculation can be performed to determine a position on an infrared camera image of a perspective projection of each voxel of a pulse volume. With a projection image generated in this manner based on perspective projection, a projection method to a two-dimensional coordinate is approximately consistent with that of an infrared camera image.

Figure 7:
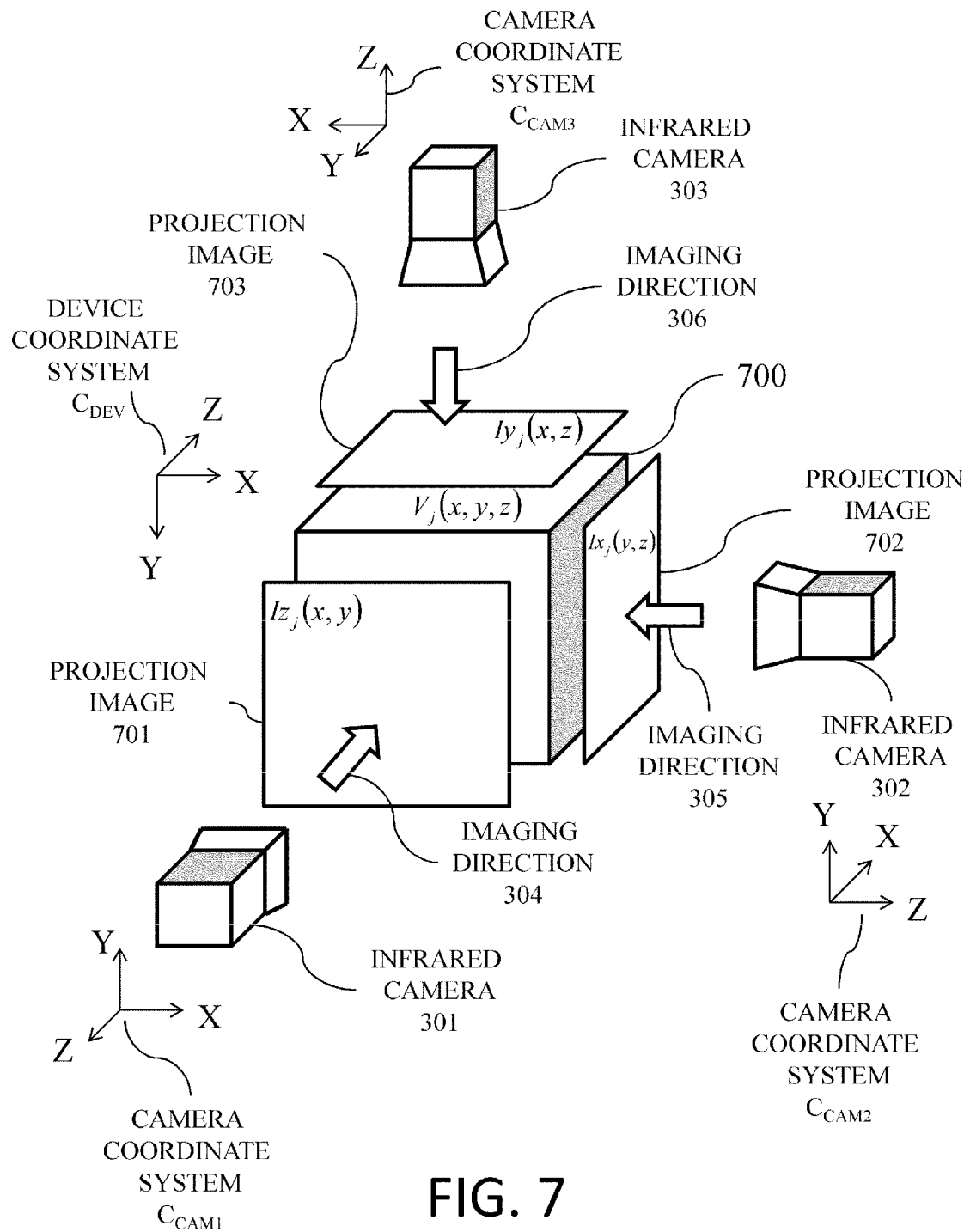
FIG. 7 is a diagram showing a spatial relationship among infrared cameras, projection images, and a pulse volume.

FIG. 7 shows a spatial relationship among the respective infrared cameras, a pulse volume, and generated projection images. A pulse volume 700 represents volume data in a three-dimensional space expressed by the X, Y, and Z axes of the device coordinate system $C_{DEV}$. The projection image 701 is an image representing a maximum intensity projection of the volume data 700 in the Z axis direction of the device coordinate system $C_{DEV}$ or, in other words, the imaging direction 304 of the infrared camera 301, and is image data in a two-dimensional space expressed by the X and Y axes of the device coordinate system $C_{DEV}$. In a similar manner, the projection image 702 is two-dimensional image data expressed by the Y and Z axes, and the projection image 703 is two-dimensional image data expressed by the Z and X axes.

In the present embodiment, the projection images 702, 703, and 701 generated by respectively performing perspective projections of volume data in the X, Y, and Z directions of the device coordinate system $C_{DEV}$ will be respectively expressed as Ipx_i, Ipy_i, and Ipz_i ($1 \leq i \leq N\_pulse$). In this case, the projection image Ipx_i is an image projected in a same direction as the imaging direction of the infrared camera image$_{CAM2}$, the projection image Ipy_i is an image projected in a same direction as the imaging direction of the infrared camera image$_{CAM3}$, and the projection image Ipz_i is an image projected in a same direction as the imaging direction of the infrared camera image$_{CAM1}$. In addition, in the present embodiment, when referring to a value of image data (a pixel value), the projection images Ipx_i, Ipy_i, and Ipz_i will be expressed in a function format as Ipx_i (y, z), Ipy_i (x, z), and Ipz_i (x, y).

In the present step, projection images representing projections of a pulse volume in respective directions of the X, Y, and Z axes (in the present embodiment, directions approximately consistent with imaging directions of the respective infrared cameras) by orthogonal projection are also generated. This is performed in order to enhance a shadow of a blood vessel portrayed in a pulse volume to enable a comparison between pulse volumes to be performed more easily in step S5070 (to be described later). The projection images by orthogonal projection will be respectively expressed as Iox_i, Ioy_i, and Ioz_i ($1 \leq i \leq N\_pulse$). The projection images (Ipx_i, Ipy_i, and Ipz_i) by perspective projection and the projection images (Iox_i, Ioy_i, and Ioz_i) by orthogonal projection are output to the comparing unit 1070.

(Step S5070) Acquisition of Peak Position of Degree of Similarity Between Projection Images With respect to all pairs (pairs of pulse indices) represented by comparison pair information R_j ($1 \leq j \leq N\_pair$), the comparing unit 1070 compares pulse volumes adopted as a comparison pair with each other and acquires information regarding a degree of matching between the pair. Specifically, the comparing unit 1070 acquires a degree of similarity function of the projection images of both pulse volumes and a peak position of the degree of similarity function. In addition, this information is adopted as information regarding a degree of matching between the projection images or, in other words, information regarding a degree of matching of a pair of pulse volumes on which the projection images are based. This process corresponds to a comparison process of images portraying a local area of the object.

As the degree of similarity function, degree of image similarity functions are used which set projection images (Iox_i, Ioy_i, and Ioz_i) representing orthogonal projections of the pulse volumes forming a comparison pair as processing objects and which have, as values, degrees of similarity when the projection images are overlapped with each other while shifting positions thereof. Specifically, the three degree of similarity functions below are acquired for a projection image of each of the pairs (expressed as R_j, 1 and R_j, 2) of pulse indices represented by the comparison pair information R_j.

[Math. 1]

$$FLX_j(y,z) = f_{simil}(Iox_{R_{j,1}}, Iox_{R_{j,2}}, y, z) \qquad (1)$$

$$FLY_j(x,z) = f_{simil}(Ioy_{R_{j,1}}, Ioy_{R_{j,2}}, x, z) \qquad (2)$$

$$FLZ_j(x,y) = f_{simil}(Ioz_{R_{j,1}}, Ioz_{R_{j,2}}, x, y) \qquad (3)$$

where f_simil (I1, I2, x, y) represents a function that calculates a degree of similarity between images I1 and I2 when a relative position of the image I2 is translated by (x, y) with respect to the image I1. For example, an arbitrary degree of similarity measure such as a sum of squared difference (SSD), a sum of absolute difference (SAD), a mutual information amount, and a cross-correlation can be applied. In this case, the function f_simil is assumed to return a high value as a function value when the degree of similarity between images is high.

Specifically, the acquisition of degree of similarity functions (FLX_j, FLY_j, and FLZ_j) refers to acquisition of a function value when an amount of translation (x, y, z) that is an argument of each function is discretely changed within a prescribed range. Signal measurement positions of the respective pulse volumes of the comparison pair (R_j, 1 and R_j, 2) are PosS_R_j, 1 and PosS_R_j, 2 which differ from each other.

In the present step, a relative position of the signal measurement position (a position of R_j, 2 as viewed from R_j, 1: ΔPosS_j=PosS_R_j, 2−PosS_R_j, 1) is adopted as a reference value of the amount of translation, and a degree of similarity is calculated by translating a projection image in a limited range preceding and following the relative position. The reference value is a median or the like. For example, in the case of FLX_j (y, z), a set of "(2K+1)×(2K+1)"-number of values that are returned by FLX_j when values of y and z are changed both forward and backward by integer values that "range from −K to +K" with the y and z components of the relative position as centers. The set of values is data deployed on a memory array resembling a discrete image. More expansively, the degree of similarity function FLX_j (y, z) may be derived as a continuous function (or a function closely resembling a continuous function) by applying a bilinear method or a bicubic method to the set of "(2K+1)×(2K+1)"-number of values. In the present embodiment, each of the degree of similarity functions (FLX_j, FLY_j, and FLZ_j: $1 \leq j \leq N\_pair$) is acquired as a two-dimensional continuous function for each comparison pair.

Figure 8:
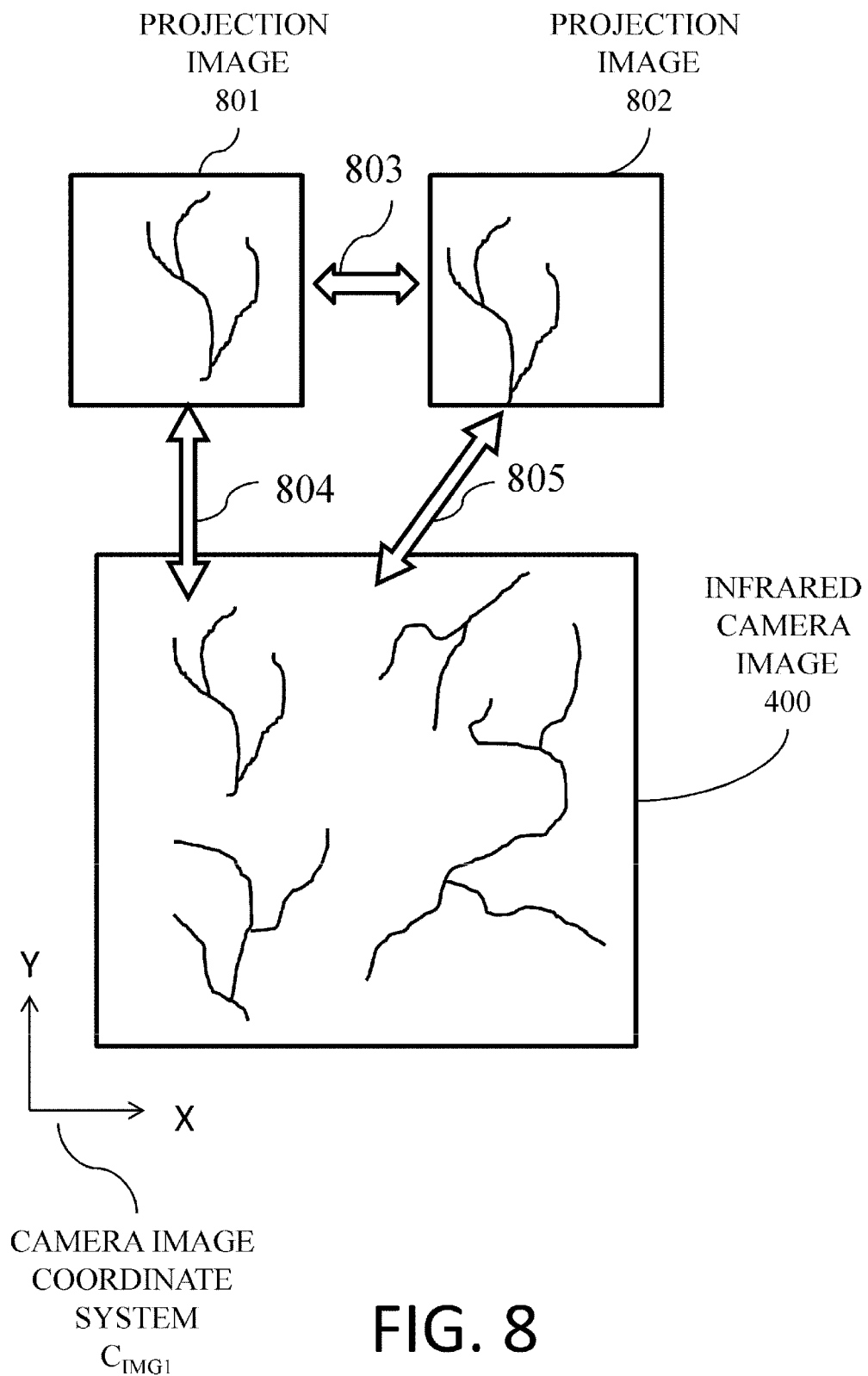
FIG. 8 is a diagram showing an example of a relation ship among images evaluated by a pulse position estimating unit.

FIG. 8 shows a relationship among images compared by the comparing unit 1070. Reference numerals 801 and 802 respectively denote projection images resulting from respectively projecting pulse volumes forming a comparison pair in the Z direction of the device coordinate system $C_{DEV}$ and include both a projection image by orthogonal projection and a projection image by perspective projection. An arrow 803 indicates that the projection image 801 (orthogonal projection) and the projection image 802 (orthogonal projection) are to be compared with each other. As shown, in the present step, a degree of similarity function is calculated by comparing a similarity of blood vessel orientation between projection images that form a comparison pair.

Next, the comparing unit 1070 calculates a position where the degree of similarity function regarding each of the comparison pairs takes a maximum value (a degree of similarity peak position). Specifically, for each of the degree of similarity functions (FLX_j, FLY_j, and FLZ_j: 1≤j≤N_pair) regarding each comparison pair calculated as described above, positions PosLX_j, PosLY_j, and PosLZ_j where the function value attains a maximum value is calculated as expressed by the following expression.

[Math. 2]

$$PosLX_j = (PosLX_{j,y}, PosLX_{j,z}) = \mathop{\arg\max}_{y,z}\{FLX_j(y, z)\} \qquad (4)$$

$$PosLY_j = (PosLY_{j,x}, PosLY_{j,z}) = \mathop{\arg\max}_{x,z}\{FLY_j(x, z)\} \qquad (5)$$

$$PosLZ_j = (PosLZ_{j,x}, PosLZ_{j,y}) = \mathop{\arg\max}_{x,y}\{FLZ_j(x, y)\} \qquad (6)$$

Subsequently, the comparing unit integrates these values and calculates a degree of similarity peak position PosL_j regarding the comparison pair that is a processing object as a three-dimensional vector representing an amount of translation between pulse volumes. This integration can be performed by calculating an average of maximum values obtained for each coordinate axis as expressed by the following expression.

[Math. 3]

$$PosL_j = (PosL_{j,x} \quad PosL_{j,y} \quad PosL_{j,z})^T = \left(\frac{PosLY_{j,x} + PosLZ_{j,x}}{2} \quad \frac{PosLX_{j,y} + PosLZ_{j,y}}{2} \quad \frac{PosLX_{j,z} + PosLY_{j,z}}{2}\right)^T \qquad (7)$$

According to the processes described above, the comparing unit 1070 calculates degree of similarity peak positions PosL_j (1≤j≤N_pair) regarding all comparison pairs. The value of PosL_j represents an estimation value (an individual optimum value) of a relative position between a comparison pair obtained based on local-area images. When a body motion has not occurred between a comparison pair, the value of the degree of similarity peak position PosL_j is expected to be consistent with a difference ΔPosL_j between a pair at the signal measurement positions. In other words, a difference between PosL_j and ΔPosS_j (ΔPosS_j−PosL_j) represents observation information of a (relative) body motion between the pair as acquired based on local-area images.

(Step S5080) Calculation of Peak Position of Degree of Similarity Between Projection Images and Infrared Image The comparing unit 1070 compares the respective pulse volumes and the infrared camera image with each other to acquire information regarding a degree of matching between the respective pulse volumes and the infrared camera image. In other words, degree of similarity functions of projection images Ipx_i, Ipy_i, and Ipz_i (1≤i≤N_pulse) representing perspective projections of the respective pulse volumes and infrared camera images $I_{CAM2}$, $I_{CAM3}$, and $I_{CAM1}$ whose projection directions respectively correspond to the projection images Ipx_i, Ipy_i, and Ipz_i (1≤i≤N_pulse) as well as peak positions of the degree of similarity functions are acquired. This information is adopted as information regarding a degree of matching between each of the projection images and the infrared camera image or, in other words, information regarding a degree of matching of each of the pulse volumes on which the projection images are based and the infrared camera image. At this point, since a blood vessel of the object is portrayed on both the projection image and the infrared camera image, a similarity of both images can be evaluated using brightness information on the blood vessel. However, the brightness of a blood vessel in the present embodiment is higher than its surroundings in a projection image and lower than its surroundings in an infrared camera image. In consideration thereof, the comparison is favorably performed by reversing brightness and darkness of the brightness value of either the infrared camera image or the projection image.

Each of the pulse volumes is an image portraying a local area of the object (a local-area image) and the infrared camera image is an image portraying an entire area of the object (a wide-area image). An objective of the present step is to compare a local-area image and a wide-area image of the object with each other by calculating degrees of similarity when the projection image of each pulse volume is overlapped with the infrared camera image while shifting a position of the projection image. First, the three degree of similarity functions below are acquired for each projection image corresponding to each pulse volume.

[Math. 4]

$$FGX_i(y,z) = f_{simil}(I_{CAM\,2}, Ipx_i, y, z) \qquad (8)$$

$$FGY_i(x,z) = f_{simil}(I_{CAM\,3}, Ipy_i, x, z) \qquad (9)$$

$$FGZ_i(x,y) = f_{simil}(I_{CAM\,1}, Ipz_i, x, y) \qquad (10)$$

where f_simil (I1, I2, x, y) represents a function similar to that used in step S5070. In the present step, the acquisition of degree of similarity functions (FGX_i, FGY_i, and FGZ_i) also refers to acquisition of a function value when an amount of translation (x, y, z) that is an argument of each function is discretely changed within a prescribed range. From the above expression, a function for calculating a degree of similarity between the projection image and the infrared camera image when a position of the projection image is translated with respect to the infrared camera image is obtained. In this case, a projection image generated by a perspective projection in an imaging direction of an infrared camera in consideration of a signal measurement position in the process of step S5060 is already expressed by a same coordinate system as the infrared camera image. Therefore, the degree of similarity in the present step is calculated using a relative position from the signal measurement position instead of an absolute position of a pulse volume as a parameter. In other words, a degree of similarity is calculated by translating the projection image within a limited ranged with (x, y, z)=(0, 0, 0), which represents a state with no positional displacement, as a reference. In the present embodiment, with respect to each of the projection images corresponding to the N_pulse-number of pulse volumes, the respective degree of similarity functions (FGX_i, FGY_i, and FGZ_i: 1≤i≤N_pulse) are acquired as two-dimensional continuous functions.

In FIG. 8, a blood vessel of the object is portrayed in the infrared camera image 400 and the projection images 801 and 802. Arrows 804 and 805 respectively denote a comparison of the projection image 801 (perspective projection) with the infrared camera image 400 and a comparison of the projection image 802 (perspective projection) with the infrared camera image 400. As shown, in the present step, a degree of similarity function is calculated by comparing a similarity of blood vessel orientation between the infrared camera image and a projection image.

Next, the comparing unit 1070 calculates a position where the degree of similarity function regarding each of the pulse volumes takes a maximum value (a degree of similarity peak position). Specifically, for each of the calculated degree of similarity functions (FGX_i, FGY_i, and FGZ_i: 1≤i≤N_pulse) regarding each pulse volume, positions PosGX_i, PosGY_i, and PosGZ_i where the function value attains a maximum value is calculated as expressed by the following expression.

[Math. 5]

$$PosGX_i = (PosGX_{i,y}, POSGX_{i,z}) = \operatorname*{argmax}_{y,z}\{FGX_i(y, z)\} \quad (11)$$

$$PosGY_i = (PosGY_{i,x}, PosGY_{i,z}) = \operatorname*{argmax}_{x,z}\{FGY_i(x, z)\} \quad (12)$$

$$PosGZ_i = (PosGZ_{i,x}, PosGZ_{i,y}) = \operatorname*{argmax}_{x,y}\{FGZ_i(x, y)\} \quad (13)$$

Subsequently, the values are integrated and a degree of similarity peak position PosG_i regarding the pulse volume that is a processing object is calculated as a three-dimensional vector representing an amount of translation from the signal measurement position of the pulse volume. This integration can be performed in a similar manner to step S5070 by calculating an average of maximum values obtained for each coordinate axis as expressed by the following expression.

[Math. 6]

$$PosG_i = (PosG_{i,x} \quad PosG_{i,y} \quad PosG_{i,z})^T = \quad (14)$$
$$\left( \frac{PosGY_{i,x} + PosGZ_{i,x}}{2} \quad \frac{PosGX_{i,y} + PosGZ_{i,y}}{2} \quad \frac{PosGX_{i,z} + PosGY_{i,z}}{2} \right)^T$$

According to the processes described above, the comparing unit 1070 calculates degree of similarity peak positions PosG_i (1≤i≤N_pulse) of all projection images with respect to the infrared camera image. Moreover, when a body motion has not occurred in the pulse volume, the value of the degree of similarity peak position PosG_i is expected to be (0, 0, 0). In other words, a sum of signal measurement positions PosS_i and PosG_i represents an estimated position (an individual optimum value) of the pulse volume based on a wide-area image. In addition, the value of PosG_i itself represents observation information of (an absolute) body motion in the pulse volume acquired based on a wide-area image.

(Step S5090) Estimation of Body Motion for Each Pulse Based on Two Types of Peak Positions The pulse position estimating unit 1080 calculates a pulse position estimation amount Pos_i (1≤i≤N_pulse) from the degree of similarity peak position PosL_j (1≤j≤N_pair) obtained in S5070 and the degree of similarity peak position PosG_i (1≤i≤N_pulse) obtained in S5080. In other words, positions of all pulse volumes are comprehensively optimized while maintaining, to the greatest extent possible, an individual optimum value regarding relative positions between local-area images (pulse volumes) of the object and an individual optimum value regarding a position of each local-area image with respect to a wide-area image (an infrared camera image) of the object. The pulse position estimation amount Pos_i is a value which satisfies, to the greatest extent possible, both a most similar positional relationship among comparisons of pulse volumes (arrow 803: first comparison) and a most similar positional relationship among comparisons between the infrared camera image and the pulse volumes (arrows 804 and 805: second comparison).

Specifically, a cost function E is defined as follows and a position of each pulse volume is optimized so as to reduce the cost function E.

[Math. 7]

$$E = \alpha \sum_{j=1}^{N_{pair}} EL_j(PosL_j, Pos_{R_{j,1}}, Pos_{R_{j,2}}) + \quad (15)$$
$$(1-\alpha) \sum_{i=1}^{N_{pulse}} EG_i(PosG_i, Pos_i),$$

where α denotes a weight coefficient (where κ≤α≤1) for balancing a first term (first comparison) and a second term (second comparison). In the present embodiment, α=0.5 is assumed. A function EL_j is a function for calculating a cost due to a positional displacement between local-area images of the object. This value is calculated based on the degree of similarity peak position PosL_j, a difference between relative values of position estimation amounts of the two pulse volumes which form the comparison pair (in other words, Pos_R_j, 2−Pos_R_j, 1), and the like. In other words, this is a function having, as cost, an amount of displacement of an estimated value from an individual optimum value of a relative position between local-area images of the object.

Specifically, the function EL_j is calculated according to the expression below.

[Math. 8]

$$EL_j(PosL_j, Pos_{R_{j,1}}, Pos_{R_{j,2}}) = (PosL_{j,x} - (Pos_{b_j,x} - Pos_{a_j,x}))^2 + (PosL_{j,y} - (Pos_{b_j,y} - Pos_{a_j,y}))^2 + (PosL_{j,z} - (Pos_{b_j,z} - Pos_{a_j,z}))^2 \quad (16)$$

where a_j denotes a first pulse index value R_j, 1 of a j-th comparison pair and b_j similarly denotes a second pulse index value R_j, 2 of the j-th comparison pair.

In addition, a function EG_i is a function for calculating a cost due to a positional displacement of a local-area image with respect to a wide-area image of the object. This value is calculated based on a difference between an estimated position of a pulse volume (in other words, PosS_i+PosG_i)

which is solely based on the degree of similarity peak position PosG_i and a position estimation amount Pos_i of the pulse volume, and the like. In other words, this is a function having, as cost, an amount of displacement of an estimated value from an individual optimum value of a position of a local-area image with respect to a wide-area image of the object. Specifically, the function EG_i is calculated according to the expression below.

[Math. 9]

$$EL_i(PosG_i, Pos_i) = ((PosS_{i,x} + PosG_{i,x}) - Pos_{i,x})^2 + ((PosS_{i,y} + PosG_{i,y}) - Pos_{i,y})^2 + ((PosS_{i,z} + PosG_{i,z}) - Pos_{i,z})^2 \quad (17)$$

Moreover, various known methods including a general nonlinear optimization method by repetitive calculation such as a steepest descent method and Newton's method and a linear optimization method can be used to optimize the cost function E. In addition, a definition of the cost function E is not limited to the definition provided above. For example, while expressions 16 and 17 use an L2 norm as an evaluation measure of an amount of displacement, other distance measures such as an L1 norm may be used. Furthermore, for example, regularization may be applied to a fluctuation (motion) of a position of each pulse volume in addition to expression 15. Generally, it is assumed that a body motion during imaging is not excessively large but continuous and gradual. Therefore, when optimizing a position of a pulse volume, a regularization process is performed in order to prevent a motion deviating from this assumption from being calculated. Examples of a regularization method include a method of multiplying a sum total of a position correction amount (a difference between the signal measurement position PosS_i and the pulse position estimation amount Pos_i) by a prescribed weight coefficient and adding the result to expression 15. Other methods include a method of using a sum total of differentials (accelerations) of a correction amount and a method of using a value calculated based on a frequency component value of the correction amount. In addition, there is a method involving preparing a typical manner of fluctuation (body motion) of the object as a model and adding a difference between the model and a correction amount as a cost to expression 15.

According to the method described above, the pulse position estimating unit 1080 calculates a pulse position estimation amount Pos_i (1≤i≤N_pulse) regarding each pulse volume.

(Step S5100) Generation of Integrated Volume (Final Output Volume)

The integrated volume generating unit 1090 integrates the pulse volumes Vp_i (1≤i≤N_pulse) and generates an integrated volume Vo. At this point, the integrated volume generating unit 1090 integrates the pulse volumes Vp_i after translating the respective pulse volumes Vp_i by the pulse position estimation amount Pos_i finally obtained in step S5090 to transform the pulse volumes Vp_i to a common coordinate system. The integrated volume generating unit 1090 first calculates a range of an inclusion region that includes regions of the respective pulse volumes after translation as a range of the integrated volume. Next, in the calculated inclusion region, voxel values of the respective pulse volumes having been transformed to the same coordinate are averaged to generate the integrated volume. The integrated volume is transmitted to the display control unit 1100 and, at the same time, stored in a storage medium (not shown).

(Step S5110) Display

The display control unit 1100 outputs information on an output image Vo to the display apparatus 130 and causes the display apparatus 130 to display the output image Vo. Examples of display methods include a method of displaying a two-dimensional image (projection image) obtained by subjecting the integrated volume to a maximum intensity projection process in a prescribed direction, a method involving volume rendering of the integrated volume, and a method of displaying a tomographic image that represents the integrated volume having been sliced at an arbitrary section.

As described above, with the image processing apparatus according to the present embodiment, in a correction process of a body motion that occurs during imaging, local-area images of the object are compared with each other and, at the same time, the local-area images are compared with an image capturing the entire object. Accordingly, an image can be acquired which better conforms to an intrinsic anatomical structure of the object and in which distortion is suppressed as a whole.

(Modification 1-1): Projection Images Representing Changed Amounts of Translation May be Respectively Generated In step S5080, degree of similarity functions are calculated while translating positions of the same projection images Ipx_i, Ipy_i, and Ipz_i generated in step S5060. However, when a position of a pulse volume in the device coordinate system $C_{DEV}$ changes, a projection image generated by perspective projection also changes. In consideration thereof, in step S5060, with respect to each pulse volume Vi (1≤i≤N_pulse), an amount of translation (x, y, z) from a signal measurement position is discretely changed within a prescribed range in the device coordinate system $C_{DEV}$ to generate projection images in the respective directions.

In addition, in step S5080, an amount of translation (x, y, z) from a signal measurement position when acquiring each degree of similarity function is defined on the device coordinate system $C_{DEV}$. Furthermore, when calculating a degree of similarity corresponding to an individual amount of translation, the degree of similarity is calculated after selecting a projection image corresponding to the amount of translation. For example, when calculating a degree of similarity function FGX_j (y_k, z_k) in step S5080, a projection image corresponding to the amount of translation (0, y_k, z_k) generated in step S5060 is selected as a projection image Ipx_i for which a degree of similarity to the infrared camera image $I_{CAM2}$ is to be calculated. Degree of similarity functions can also be calculated for other directions. With the method according to the present modification, a degree of similarity that better reflects a position of a pulse volume can be acquired.

(Modification 1-2): Infrared Camera Need not be Orthogonal to Device Coordinate System In the first embodiment described above, imaging directions of the three infrared cameras are consistent with coordinate axes of the device coordinate system. However, imaging directions are not limited thereto as long as an entire contour of the object is included in an infrared camera image. For example, there may be cases where, depending on a structure of the apparatus, the object cannot be arranged in the Z axis direction (device coordinate system $C_{DEV}$) of the infrared camera 301. In such a case, a direction in which the infrared camera 301 faces is set to a direction in which the Z axis is rotated by 45 degrees around the Y axis. A vector representing this direction will be defined as d.

The projection direction of the projection image generated in step S5060 is consistent with an imaging direction of the infrared camera. In consideration thereof, by projecting a pulse volume in the direction of the vector d described above by perspective projection, a projection image Id_i is generated instead of Iz_i that is a projection image in the Z direction. Next, in the calculation of degree of similarity functions in steps S5070 and S5080, FLD_j (x, y, z) and FGD_i (x, y, z) expressed by the following expression are acquired instead of the degree of similarity functions FLZ_j (x, y) and FGZ_i (x, y) corresponding to the projection image Iz_i in the Z direction.

[Math. 10]

$$FLD_j(x,y,z)=f_{simil}(Id_{R_{j,1}}, Id_{R_{j,2}}, x, y, z) \quad (18)$$

$$FGD_i(x,y,z)=f_{simil}(I_{CAM_i}, Id_i, x, y, z) \quad (19)$$

where f_simil (I1, I2, x, y, z) represents a function that calculates a degree of similarity between images I1 and I2 when a relative position of the image I2 is translated by (x, y, z) with respect to the image I1. This function has one more translational axis than f_simil (I1, I2, x, y) described in step S5070. The amount of translation (x, y, z) in this case is defined in advance on the device coordinate system $C_{DEV}$. In order to acquire the functions FLD_j (x, y, z) and FGD_i (x, y, z), degrees of similarity are calculated while discretely changing a value of the amount of translation (x, y, z) within a prescribed range. However, a relative position of a projection image is not changed by a translation in a direction parallel to the vector d. In consideration thereof, the amount of translation (x, y, z) is changed on a plane orthogonal to the vector d within a prescribed region (for example, a rectangular region) with a position where the amount of translation is 0 as a reference. Accordingly, the degree of similarity functions FLD_j (x, y, z) and FGD_i (x, y, z) are acquired. By performing similar processes for the other infrared cameras 302 and 303, an infrared camera image and pulse volumes can be compared with each other even when the device coordinate system and an imaging direction of an infrared camera are not consistent with each other.

(Modification 1-3): Degree of Similarity Function Need not be Degree of Image Similarity Using Brightness Value In the first embodiment described above, as the process performed in step S5060, a MIP image is generated as a projection image of a pulse volume. However, for example, a MinP image (a minimum intensity projection image) may be generated instead of a MIP image. Alternatively, both a MIP image and a MinP image may be generated, and either both images or whichever image is more favorable of the two images may be used in subsequent processes.

In addition, in steps S5070 and S5080 in the first embodiment described above, degree of similarity functions between images are obtained based on degrees of similarity between pixel values. However, for example, an anatomical characteristic such as a blood vessel of the object may be extracted by image processing and a degree of similarity function may be acquired based on a degree of matching of a distribution or a position of the anatomical characteristic. In this case, the characteristic may be extracted using a known image processing technique such as edge detection and corner detection. Alternatively, a higher-order local-area image characteristic such as a SIFT characteristic and a SURF characteristic which are commonly used in the technical fields of computer vision and the like may be used. According to these methods, a degree of similarity function that is more robust with respect to a difference in brightness distributions between images, noise contamination, and the like can be acquired. Furthermore, in step S5070, original pulse volumes may be compared without any modification with each other instead of comparing projection images.

(Modification 1-4): Rotation May be Included in Addition to Translation

In the first embodiment described above, in steps S5070 and S5080, degree of similarity functions regarding an amount of translation between pulse volumes and an amount of translation of a projection image with respect to an infrared camera image are acquired. However, as a positional relationship, rotation may be considered in addition to translation. In this case, the degree of similarity functions acquired in steps S5070 and S5080 become degree of similarity functions regarding an amount of translation on a projection plane and an amount of rotation within the projection plane between the respective projection images. In this case, instead of calculating a peak position as a three-dimensional vector, a peak position is calculated as, for example, a rigid transformation matrix that is maximized at a degree of similarity function between projection images and a rigid transformation matrix that is maximized at a degree of similarity function between an infrared camera image and a projection image.

In addition, in step S5090, a translation and a rotation (in other words, a rigid transformation) of each pulse volume is calculated instead of a pulse position estimation amount. This calculation process can be performed by optimizing a cost function having the following two costs. A first cost is a cost representing consistency between a matrix representing a difference in rigid transformations between projection images and the rigid transformation matrix between projection images obtained in step S5070. A second cost is a cost representing consistency between a matrix representing a difference in rigid transformations between an infrared camera image and a projection image and the rigid transformation matrix between the infrared camera image and the projection image obtained in step S5080.

Furthermore, in step S5100, pulse volumes are integrated based on the rigid transformations. However, when acquiring degree of similarity functions including rotation in steps S5070 and S5080, the fact that rotations of a projection image on the respective projection planes are not mutually independent is desirably taken into consideration. In other words, an in-plane rotation of a projection image on a given projection plane signifies a rotation around an axis that is a normal direction of the projection plane of a corresponding pulse volume. This rotation cannot always be expressed as a translation or an in-plane rotation with respect to a projection image on a different projection plane. Therefore, a projection image on another projection plane is desirably re-generated in consideration of this rotation.

According to the method described above, an integrated volume with higher image quality can be generated when a motion of the object during imaging includes rotation in addition to translation.

(Modification 1-5): A Projection Image in One Axis Direction May be Omitted

In the first embodiment described above, projection images that are projected in three orthogonal directions are generated in the process performed in step S5060. However, for example, projection images may only be generated in the Z axis direction and the Y axis direction, and projection in the X axis direction may be omitted. Even in this case, information on a translation on an XY plane can be acquired based on a projection image in the Z axis direction and information on a translation on an XZ plane can be acquired based on a projection image in the Y axis direction. Therefore, information on motion in all axial directions can be acquired. According to this method, calculation cost can be reduced as compared to the first embodiment. In this case, only two infrared cameras in the Z axis direction and the Y axis direction need be provided.

In addition, when a restriction regarding a body motion of the object can be assumed in advance, the calculation cost can be further reduced. For example, when a body motion of the object does not occur (or is extremely small) in the Z axis direction due to a posture of the object during photography, a physical constraint imposed by the photographic apparatus itself, or the like, only a projection image in the Z axis direction is generated and processing is performed solely on a body motion in the XY direction. Accordingly, calculation on a direction in which a body motion does not occur can be omitted. In this case, only one infrared camera in the Z axis direction need be provided. In addition, a configuration may be adopted in which a comparison between local-area images (between a comparison pair) as a process for obtaining a detailed body motion is performed with respect to a plurality of directions and a comparison between a wide-area image and a local-area image as a process for maintaining overall consistency is only performed with respect to one direction (for example, the XY direction). Accordingly, the effect of the invention can be obtained with a minimal apparatus configuration (one infrared camera) while performing three-dimensional body motion correction.

Furthermore, when it is assumed that a body motion of the object only occurs in one axis direction, processing can be performed only using a projection image that is projected in a direction that enables motion on the axis to be observed. For example, when the object only moves in the X axis direction, since a body motion in the X axis direction can be calculated solely based on a projection image in the Y axis direction or the Z axis direction, calculation cost can be reduced.

Second Embodiment

A second embodiment of the present invention will be described. In the first embodiment, both a comparison between respective measured photoacoustic images and a comparison between the respective photoacoustic images and an infrared camera image are performed to estimate and correct a body motion (using a cost function that takes these relationships into consideration at the same time). In the second embodiment, first, a first estimation is performed by a comparison between respective measured photoacoustic signals and, next, a second estimation is performed by comparing a result of correction performed based on the first estimation with an infrared camera image. Therefore, for the second estimation that is directly linked to a final result, an estimation that only targets an infrared camera image is performed. As a result, a photoacoustic image that better conforms to an infrared camera image can be acquired.

(Apparatus Configuration)

Figure 9:
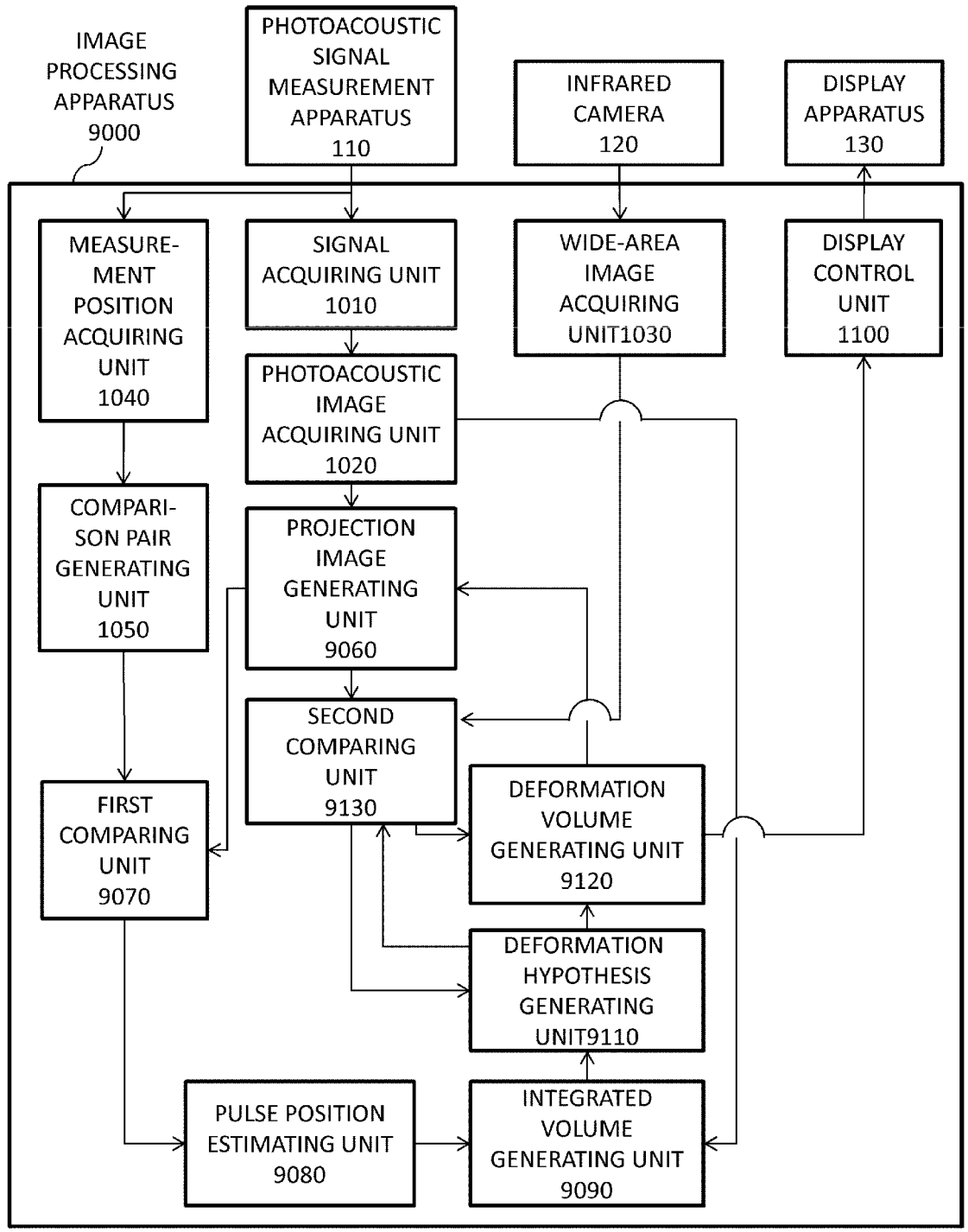
FIG. 9 is a diagram showing a functional configuration of an image processing apparatus according to a second embodiment.

Hereafter, a configuration of a photoacoustic apparatus according to the present embodiment will be described with reference to FIG. 9. It should be noted that components similar to those of the first embodiment will be denoted by the same reference numerals and a description thereof will be omitted.

An image processing apparatus 9000 includes a signal acquiring unit 1010, a photoacoustic image acquiring unit 1020, a wide-area image acquiring unit 1030, a measurement position acquiring unit 1040, a comparison pair generating unit 1050, and a projection image generating unit 9060. The image processing apparatus 9000 further includes a first comparing unit 9070, a pulse position estimating unit 9080, an integrated volume generating unit 9090, a deformation hypothesis generating unit 9110, a deformation volume generating unit 9120, a second comparing unit 9130, and a display control unit 1100.

The projection image generating unit 9060 respectively generates projection images (or MIP images: hereinafter referred to as pulse projection images) from a plurality of pulse volumes acquired from the photoacoustic image acquiring unit 1020 and outputs the plurality of generated pulse projection images to the first comparing unit 9070. In addition, the projection image generating unit 9060 respectively generates projection images (hereinafter referred to as deformation projection images) from a plurality of deformation volumes acquired from the deformation volume generating unit 9120 and outputs the plurality of generated deformation projection images to the second comparing unit 9130.

Based on comparison pair information acquired from the comparison pair generating unit 1050, the first comparing unit 9070 compares pixel values or the like of pulse projection images of the pulse volumes forming the pair as a process of comparing the pulse volumes forming the pair (first comparison) to calculate information regarding a degree of matching between the pair. Subsequently, the first comparing unit 9070 outputs the calculated information to the pulse position estimating unit 9080.

The pulse position estimating unit 9080 calculates estimation values of positions of the respective pulse volumes (pulse position estimation amounts) based on the information regarding the degree of matching between the pair as calculated by the first comparing unit 9070 and outputs the pulse position estimation amounts to the integrated volume generating unit 9090.

The integrated volume generating unit 9090 generates an integrated volume that integrates pulse volumes based on the pulse position estimation amounts, outputs the integrated volume to the deformation hypothesis generating unit 9110, and stores the integrated volume in a storage medium (not shown).

With an estimated deformation parameter calculated by the second comparing unit 9130 (to be described later) as a reference, the deformation hypothesis generating unit 9110 generates a plurality of hypotheses of deformation parameters (hereinafter, referred to as deformation hypotheses) for deforming the integrated volume acquired from the integrated volume generating unit 9090. Subsequently, the deformation hypothesis generating unit 9110 outputs the plurality of generated deformation hypotheses to the deformation volume generating unit 9120 and the second comparing unit 9130.

The deformation volume generating unit 9120 deforms the integrated volume stored in the storage medium to generate a plurality of deformation volumes for each of the plurality of deformation hypotheses acquired from the deformation hypothesis generating unit 9110 and outputs the generated deformation volumes to the projection image generating unit 9060. In addition, when command information for completing the deformation (deformation completion command) and a final deformation parameter are acquired from the second comparing unit 9130 (to be described later), the deformation volume generating unit 9120 generates an output volume by deforming the integrated volume based on the final deformation parameter. The generated output volume is output to the display control unit 1100.

As a comparison process (second comparison) of each of the plurality of pulse volumes generated by the photoacoustic image acquiring unit 1020 and the infrared camera image acquired from the wide-area image acquiring unit 1030, the second comparing unit 9130 compares an integrated image of the group of pulse volumes and the infrared camera image with each other. More specifically, the second comparing unit 9130 compares pixel values or the like of the infrared camera image and the plurality of deformation projection images (derived from the integrated image of the group of pulse volumes) acquired from the projection image generating unit 9060 with each other and calculates information regarding a degree of matching between the images. Furthermore, the second comparing unit 9130 calculates (updates) the estimated deformation parameter based on a cost value based on the calculated information and on the deformation hypotheses acquired from the deformation hypothesis generating unit 9110 and outputs the calculated (updated) estimated deformation parameter to the deformation hypothesis generating unit 9110. In addition, based on a state of convergence of the cost value, the second comparing unit 9130 determines whether or not to complete the deformation and calculates a final deformation parameter. When the second comparing unit 9130 determines to complete the deformation, the second comparing unit 9130 outputs information on a deformation completion command and the final deformation parameter to the deformation volume generating unit 9120.

(Processing Flow)

Figure 10:
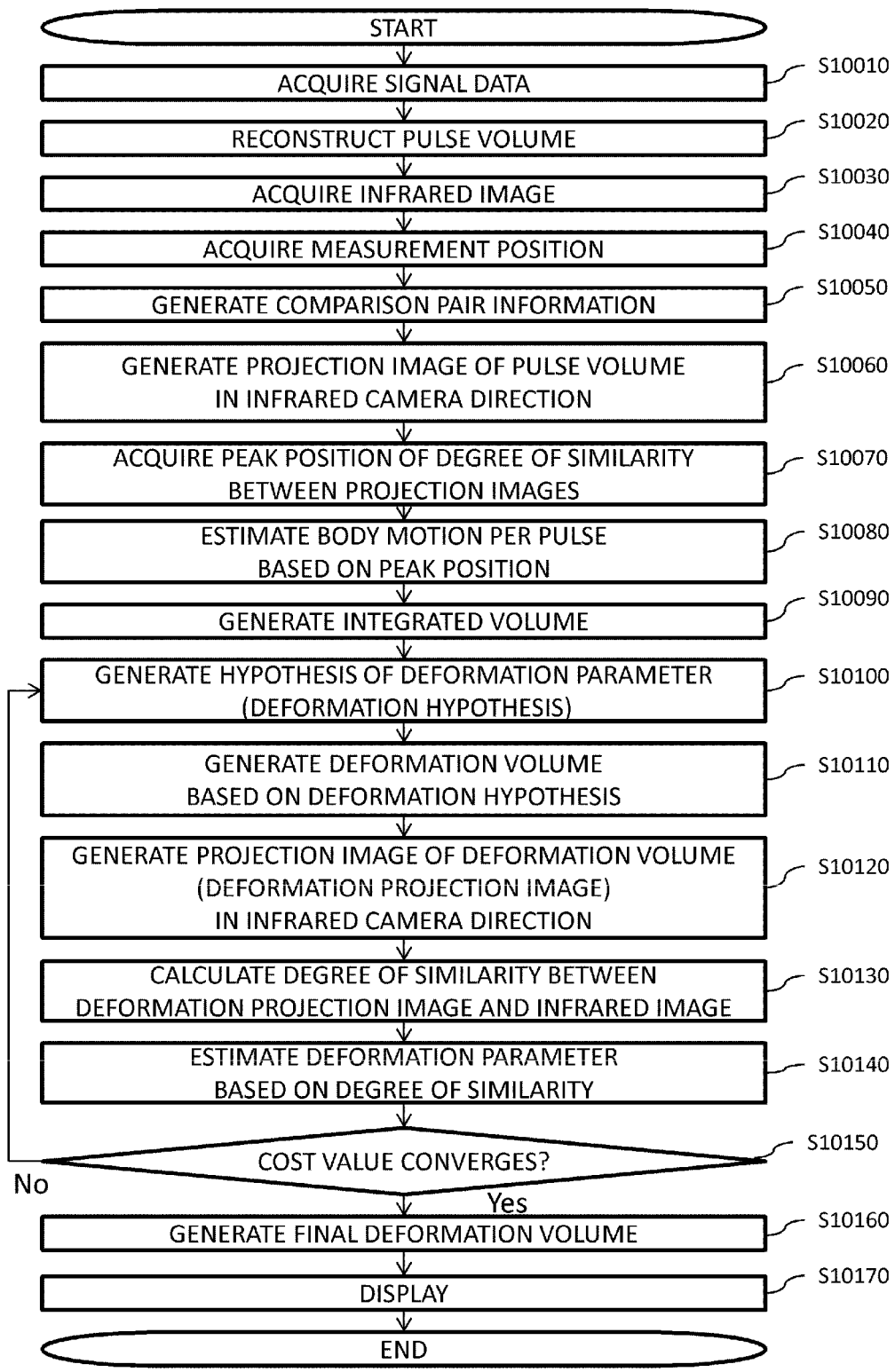
FIG. 10 is a flow chart showing an overall processing procedure according to the second embodiment.

FIG. 10 is a flow chart showing an overall procedure of processing performed by the image processing apparatus 9000.

(Steps S10010 to S10070)

In these steps, processes similar to those performed in steps S5010 to S5070 of the first embodiment are performed.

(Step S10080) Body Motion Estimation for Each Pulse Based on Peak Position of Degree of Similarity The pulse position estimating unit 9080 calculates a pulse position estimation amount Pos_i (1≤i≤N_pulse) based on a degree of similarity peak position PosL_j (1≤j≤N_pair) calculated in step S10070. In other words, positions of all pulse volumes are comprehensively optimized while maintaining, to the greatest extent possible, an individual optimum value regarding relative positions between local-area images (pulse volumes) of the object. Specifically, a cost function E is defined as follows and a position of each pulse volume is optimized so as to reduce the cost function E.

[Math. 11]

$$E = \sum_{j=1}^{N_{pair}} EL_j(PosL_j, Pos_{R_{j,1}}, Pos_{R_{j,2}}) \qquad (20)$$

The function EL_j is the same as the function EL_j defined in expression 16 in step S5090 of the first embodiment. Moreover, the cost function E according to the present embodiment corresponds to the cost function E (expression 15) in step S5090 of the first embodiment without its second term. A method of optimizing the cost function E is similar to that in step S5090 of the first embodiment.

(Step S10090) Generation of Integrated Volume

The integrated volume generating unit 1090 integrates the pulse volumes Vp_i (1≤i≤N_pulse) and generates an integrated volume Vo. This generation method is similar to that in step S5100 according to the first embodiment. The integrated volume is output to the deformation hypothesis generating unit 9110 and the deformation volume generating unit 9120 and, at the same time, stored in a storage medium (not shown).

(Step S10100) Generation of Hypothesis of Deformation Parameter

With a current value of an estimated deformation parameter as a reference, the deformation hypothesis generating unit 9110 generates a plurality of hypotheses of deformation parameters (deformation hypotheses) for deforming the integrated volume Vo acquired from the integrated volume generating unit 9090. At this point, if the present step is to be processed for the first time, the current value of an estimated deformation parameter assumes an initial value or, in other words, a value representing "no deformation". On the other hand, if the present step is to be processed for the second or subsequent time, an estimated deformation parameter p_e calculated in step S10140 (to be described later) is adopted as the current value of the estimated deformation parameter.

A deformation of the integrated volume can be calculated by, for example, free form deformation (FFD). In this case, FFD control points are arranged in a grid pattern with respect to a region including the integrated volume. In this case, a deformation parameter is expressed by a control amount of each FFD control point. Specifically, vectors of the number of elements N_grid (N_grid denotes the number of control points) representing a set of control amounts in each axial direction of (x, y, z) of a control point are respectively denoted as p_x, p_y, and p_z. In addition, a vector p={p_x, p_y, p_z} having all of the vectors as elements is defined as a deformation parameter.

Next, a method of generating a deformation hypothesis will be described. Let us now consider a case where, if a current estimated deformation parameter is denoted by p_e, a minute amount of change is respectively imparted to each element of p_e. However, if the present step is to be processed for the first time, since the estimated deformation parameter p_e is not provided by the deformation hypothesis generating unit 9110, a vector p_0 having 0 as all elements is adopted as p_e. At this point, a vector constituted by minute amounts of change imparted to the respective elements is defined as Δp.

Next, the amount of change Δp is varied so that a direction of the vector uniformly changes in a parameter space. For example, if the number of control points is N_grid, the parameter space is a space expressed as N_grid×three dimensions. At this point, a given set of the amount of change Δp is generated as a set of vectors representing a movement by a prescribed value d of only an element of a specific axis in the parameter space. By performing this process on all axes (N_grid×3) in the parameter space, an amount of change Δp_i (1≤i≈N_grid×3) for (N_grid×3)-number of patterns can be acquired. In other words, a set of Δp_i corresponding to the number of elements in the vector is acquired. Moreover, a combination of the amount of change Δp is not limited to this example as long as the amount of change Δp is varied so that a direction of the vector uniformly changes in the parameter space.

Subsequently, a deformation parameter p_i is generated by adding the amount of change Δp_i to the current estimated deformation parameter p_e (when the present step is processed for the first time, p_i=Δp_i). At this point, the number of generated deformation parameters is defined as N_hypo (in the present embodiment, N_hypo=N_grid×3). In this case, a combination of the set of generated deformation parameters {p_1, . . . , p_i, . . . , p_N_hypo} and positional information of each control point is defined as a deformation hypothesis H. Subsequently, the deformation hypothesis generating unit 9110 outputs the generated deformation hypothesis H to the deformation volume generating unit 9120 and, at the same time, stores the generated deformation hypothesis H in a storage medium (not shown). Moreover, a model expressing deformation is not limited to FFD and other methods of expressing nonlinear deformation such as thin plate spline can also be used.

(Step S10110) Generation of Deformation Volume

Based on the deformation hypothesis H acquired from the deformation hypothesis generating unit 9110, the deformation volume generating unit 9120 deforms the integrated volume Vo stored in the storage medium (not shown) to generate a deformation volume DV_i (1≤i≤N_hypo). Specifically, using an FFD deformation algorithm, the integrated volume Vo is deformed based on the positional information on the control points and the respective deformation parameters Δp_i contained in the deformation hypothesis H. The deformation volume DV_i is output to the projection image generating unit 9060.

(Step S10120) Generation of Projection Image of Deformation Volume in Infrared Camera Direction The projection image generating unit 9060 generates a deformation projection image for each imaging direction of an infrared camera from the deformation volume DV_i generated by the deformation volume generating unit 9120. This is a process which simply replaces the pulse volume in step S10060 with the deformation volume DV_i. It is assumed that a perspective projection method such as that described in "Modification 1-1" of the first embodiment is used as a projection method in the present step. The deformation projection images respectively generated by projection in the X, Y, and Z directions of the device coordinate system $C_{DEV}$ are respectively denoted as DIpx_i, DIpy_i, and DIpz_i (1≤i≤N_hypo).

(Step S10130) Calculation of Degree of Similarity Between Deformation Projection Images and Infrared Image The second comparing unit 9130 calculates degrees of similarity between the deformation projection images DIpx_i, DIpy_i, and DIpz_i (1≤i≤N_hypo) and infrared camera images $I_{CAM2}$, $I_{CAM3}$, and $I_{CAM1}$ in projection directions to which the deformation projection images respectively correspond. The calculated degrees of similarity are respectively denoted as Sx_i, Sy_i, and Sz_i. At this point, a degree of similarity measure similar to that of step S5070 of the first embodiment can be applied.

(Step S10140) Estimation of Deformation Parameter Based on Degree of Similarity

The second comparing unit 9130 calculates (updates) an estimated deformation parameter based on the degrees of similarity Sx_i, Sy_i, and Sz_i (1≤i≤N_hypo) calculated in step S10130. Specifically, first, based on the respective degrees of similarity Sx_i, Sy_i, and Sz_i, a value of a cost function E_s of a degree of matching between a deformation projection image and an infrared camera image when an i-th element of a deformation parameter is slightly varied (in other words, when assuming p_i) is calculated. The cost function E_s can be defined as, for example, an average value of the three degrees of similarity Sx_i, Sy_i, and Sz_i. A method of defining the cost function is not limited to this method and, for example, a maximum value among the three degrees of similarity may be adopted. Moreover, in order to express a degree of similarity when a deformation parameter p is given, the cost function E_s can be expressed as a function of p as E_s (p). Therefore, a value of the cost function corresponding to the deformation parameter p=p_i (based on the degrees of similarity Sx_i, Sy_i, and Sz_i) is expressed as E_s (p_i).

Next, a new estimated deformation parameter $p\_e^{new}$ is estimated based on the existing estimated deformation parameter p_e, the cost value E_s (p_e) of the existing estimated deformation parameter, and the values E_s (p_i) of the respective cost hypotheses calculated above. Specifically, the parameter $p\_e^{new}$ is calculated by the following expression.

[Math. 12]

$$p\_e^{new} = p\_e - \alpha\, grad\, E\_s(p\_e) == p\_e - \alpha \begin{pmatrix} E\_s(p\_1) - E\_s(p\_e) \\ \vdots \\ E\_s(p\_i) - E\_s(p\_e) \\ \vdots \\ E\_s(p\_{N\_hypo}) - E\_s(p\_e) \end{pmatrix} \quad (21)$$

where α is a small positive constant. For example, α=0.1 is adopted in the present embodiment. In addition, grad E_s denotes a gradient vector of E_s. In this case, an i-th element of a vector on a right side of expression 21 represents a value obtained by partially differentiating the cost function E_s (p) by an element i of a vector p. More specifically, the i-th element of the vector on the right side of expression 21 is a value when the partially differentiated value is approximately obtained as a difference between the cost value E_s (p_i) of the hypothesis and the cost value E_s (p_e) of the existing parameter. Accordingly, a deformation parameter $p\_e^{new}$ can be acquired which represents a variation in a direction that maximizes a gradient of the cost function E_s when the deformation parameter is varied by a minute amount in the parameter space.

Next, by subjecting the estimated deformation parameter $p\_e^{new}$ obtained above to processes similar to those of steps S10110 to S10130, a degree of similarity between a projection image of the deformation volume and an infrared camera image based on the parameter $p\_e^{new}$ is obtained. Subsequently, a cost value $E\_s\,(p\_e^{new})$ based on the degree of similarity is calculated and stored in a storage medium (not shown). At this point, it is assumed that, each time the present step is executed and a new cost value $E\_s\,(p\_e^{new})$ is calculated, the cost value is to be additionally stored in the storage medium (not shown) while retaining previous cost values. Moreover, since the cost value E_s (p_e) used in the computation of expression 21 described above is the cost value $E\_s\,(p\_e^{new})$ during an immediately previous execution of the process of the present step, the cost value can be acquired from the storage medium (not shown). However, when the process of the present step is to be performed for the first time, since the cost value E_s (p_e) has not yet been stored, a cost value E_s (p_0) with respect to an initial value p_0 must be calculated prior to the computation of expression 21.

As described above, in the present step, a process of finding a deformation parameter that moves in a gradient direction of the cost function E_s is performed. This corresponds to one step when optimizing the cost function E_s using a steepest descent method. Therefore, by repetitively performing the present step, the estimated deformation parameter $p\_e^{new}$ approaches a more favorable value. Moreover, a method of optimizing the cost function E_s is not limited to this method and, for example, Newton's method may be used.

(Step S10150) Determination of Whether Cost Function has Converged

The second comparing unit 9130 refers to preceding cost values E_s (p_e) stored in the storage medium (not shown) and determines whether or not the value has converged. When the value has converged, the second comparing unit 9130 outputs the estimated deformation parameter p_e as a final deformation parameter p_final together with information on a deformation completion command to the deformation volume generating unit 9120 and causes the processing to make a transition to step S10160. When the value has not converged, the second comparing unit 9130 outputs the estimated deformation parameter p_e to the deformation hypothesis generating unit 9110 and returns to step S10100.

Examples of a method of determining convergence include the following. As a first method, a latest value and an immediately previous value of the cost value E_s (p_e) are compared with each other, whereby convergence is determined when a difference between the values falls below a prescribed value. In addition, there is a method involving extracting cost values of a prescribed number of previous executions, respectively calculating amounts of change between two adjacent executions, and determining a convergence when an average value of the amounts of change falls below a prescribed value. Alternatively, as a simplified method, convergence is determined when the number of repetitive executions of step S10140 reaches a prescribed value.

(Step S10160) Generation of Final Deformation Volume

The deformation volume generating unit 9120 acquires information on a deformation completion command and the final deformation parameter p_final from the second comparing unit 9130 and generates an output volume V_final.

As described above, in the present embodiment, after repetitively executing steps S10100 to S10150 until a cost value of a cost function whose goal is to attain conformance to an infrared camera image converges, a final deformation volume is generated in step S10160. Accordingly, a deformation parameter that optimizes the cost function can be acquired.

(Step S10170) Display

The display control unit 1100 performs control to output information on the output volume V_final to the display apparatus 130 and display the output volume V_final on the display apparatus 130. The present process is similar to that of step S5110 according to the first embodiment.

As described above, with the image processing apparatus according to the present embodiment, by estimating a deformation of a pulse volume while solely targeting an infrared camera image in an estimation directly linked to a final result of motion correction of an object, a photoacoustic image better conforming to the object portrayed in the infrared camera image can be acquired.

Third Embodiment

A third embodiment of the present invention will be described. In the first and second embodiments, an infrared camera image is used as a wide-area image. In the third embodiment, a depth image of an object is used as a wide-area image. Accordingly, information of a photoacoustic image which is volume data can be compared in a three-dimensional space instead of in a two-dimensional space which degenerates the information of a photoacoustic image.

(Apparatus Configuration)

Figure 11:
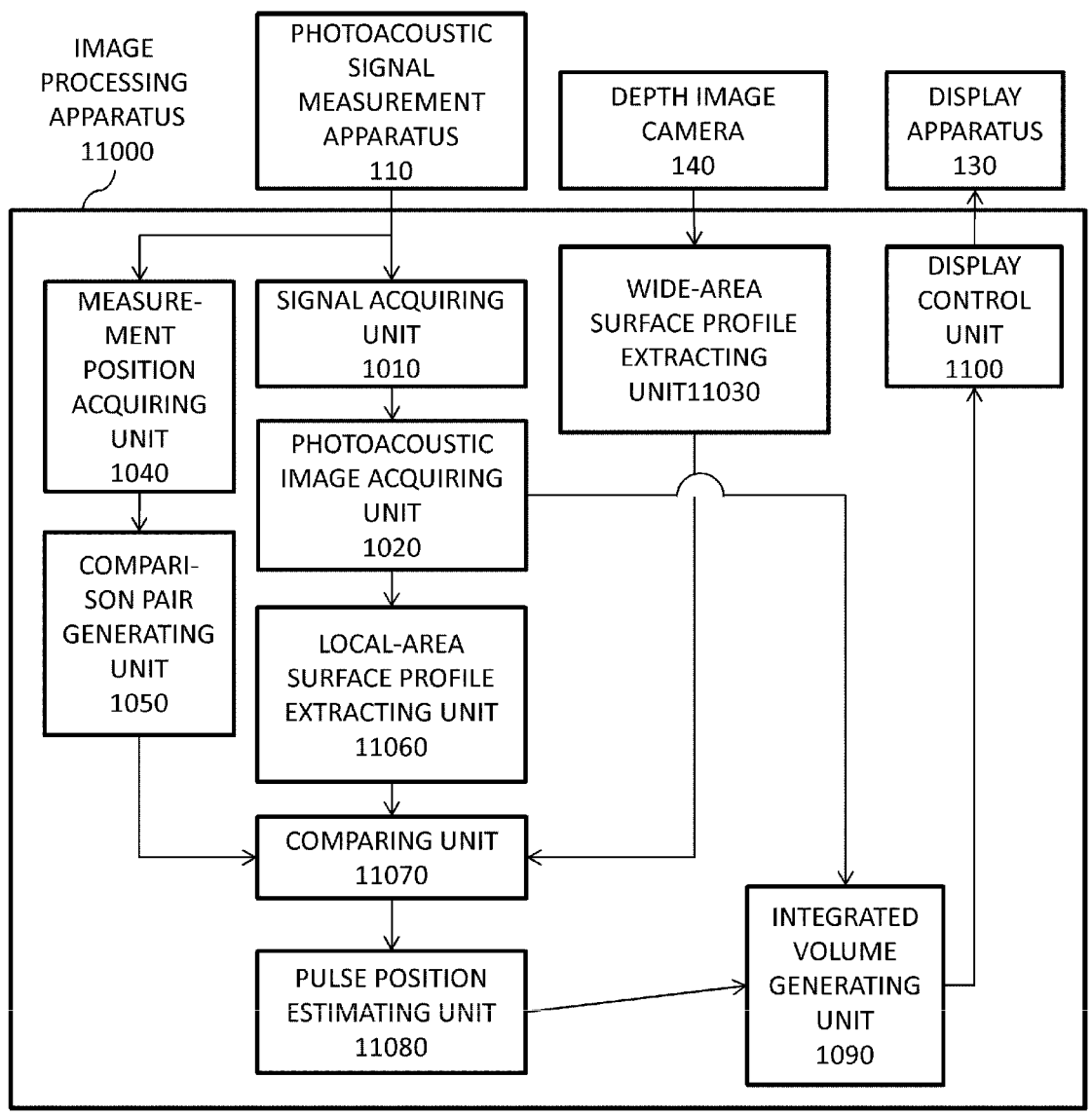
FIG. 11 is a diagram showing a functional configuration of an image processing apparatus according to a third embodiment.

Hereafter, a configuration of a photoacoustic apparatus according to the present embodiment will be described with reference to FIG. 11. Components similar to those of the first embodiment will be denoted by the same reference numerals and a description thereof will be omitted.

A depth image camera 140 is a (time of flight) camera which projects a laser on an object and measures a range to the object based on the time required by the projected laser to return after being reflected off of the object. Accordingly, a three-dimensional surface profile of the object is obtained in the form of a depth image. The depth image camera 140 is installed at a position that enables the entire object to be measured. An obtained depth image (denoted as $I_{RNG}$) is input to an image processing apparatus 11000.

Moreover, the depth image camera 140 has already been calibrated with respect to the device coordinate system $C_{DEV}$ and information regarding coordinate transformations as well as internal parameters of the camera are stored in the image processing apparatus 11000 as known information. Each pixel value on the depth image $I_{RNG}$ represents a range to a point in a space existing on alight of sight that passes through each pixel. In other words, a coordinate of a point corresponding to each pixel in a three-dimensional depth image camera coordinate system $C_{RNG}$ can be obtained from a coordinate value and a pixel value of each pixel. In addition, known methods can be used for transformation from the depth image camera coordinate system $C_{RNG}$ to the device coordinate system $C_{DEV}$ (hereinafter, referred to as $T_{RtoD}$).

The image processing apparatus 11000 includes a signal acquiring unit 1010, a photoacoustic image acquiring unit 1020, a wide-area surface profile acquiring unit 11030, a measurement position acquiring unit 1040, a comparison pair generating unit 1050, and a local-area surface profile extracting unit 11060. The apparatus further includes a comparing unit 11070, a pulse position estimating unit 11080, an integrated volume generating unit 1090, and a display control unit 1100.

The wide-area surface profile acquiring unit 11030 acquires a depth image captured by the depth image camera 140 as a wide-area image, generates three-dimensional point group information representing a surface profile over a wide area of the entire object from the depth image (hereinafter, referred to as a wide-area surface profile), and outputs the wide-area surface profile to the comparing unit 11070.

The local-area surface profile extracting unit 11060 extracts a surface profile of the object from a pulse volume portraying a FOV that is a local area of the object (hereinafter, referred to as a local-area surface profile) and outputs the local-area surface profile to the comparing unit 11070.

Based on comparison pair information, as a process of comparing pulse volumes forming the pair (first comparison), the comparing unit 11070 performs a process of comparing voxel values or the like between the pair and calculates a degree of similarity between the pair as information regarding a degree of matching between the pair. In addition, as a process of comparing each pulse volume and a depth image with each other (second comparison), the comparing unit 11070 compares the local-area surface profile acquired from the local-area surface profile extracting unit 11060 and the wide-area surface profile acquired from the wide-area surface profile acquiring unit 11030 with each other and calculates information regarding a degree of matching. Furthermore, the comparing unit 11070 outputs the calculated information regarding the degree of matching to the pulse position estimating unit 11080.

The pulse position estimating unit 11080 calculates estimation values of positions of the respective pulse volumes (pulse position estimation amounts) based on both the information regarding the degree of matching between the pair and the information regarding the degree of matching between the respective pulse volumes and the depth image input from the comparing unit 11070. The calculated estimation values are output to the integrated volume generating unit 1090.

(Processing Flow)

Figure 12:
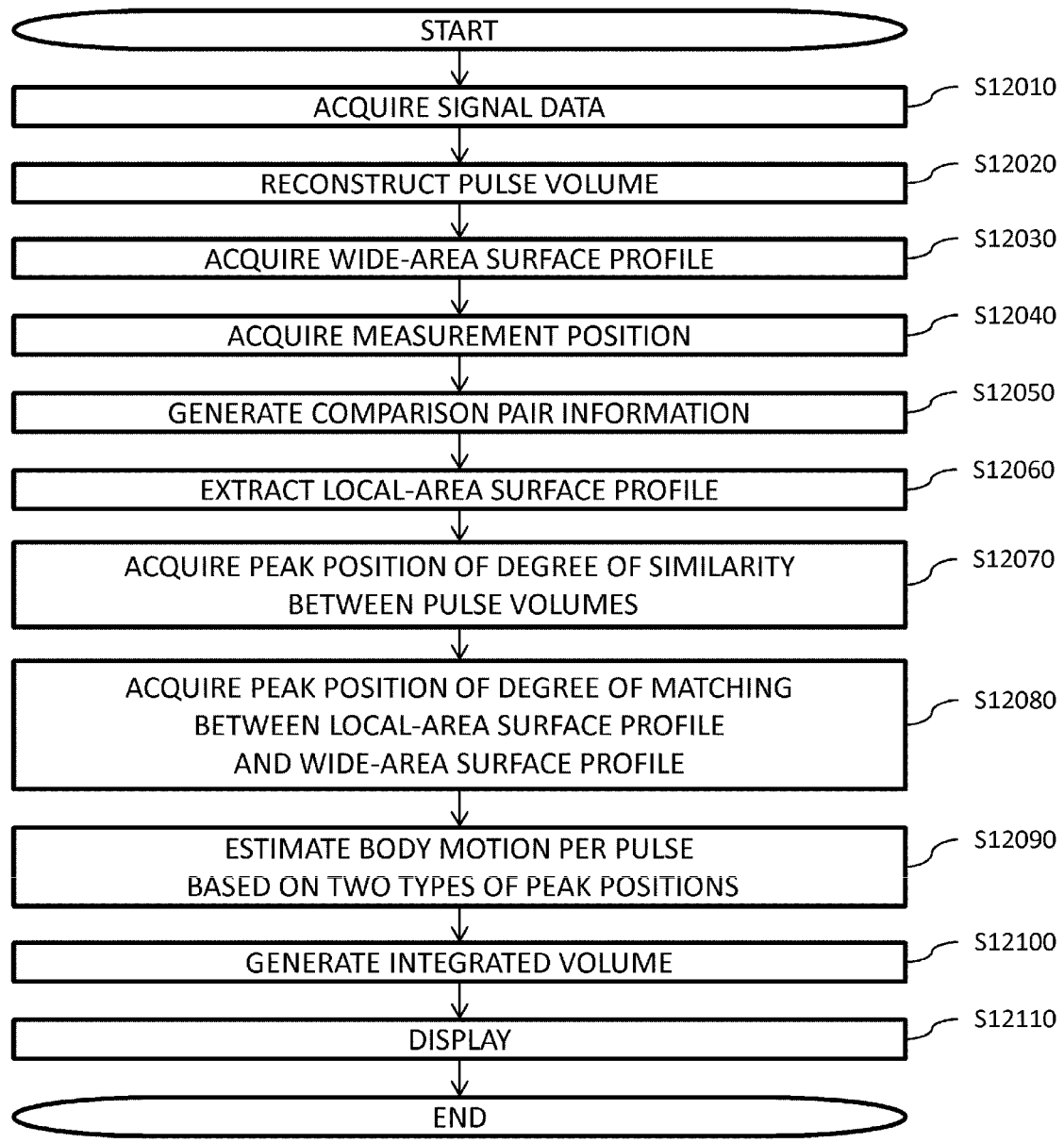
FIG. 12 is a flow chart showing an overall processing procedure according to the third embodiment.

FIG. 12 is a flow chart showing an overall procedure of processing performed by the image processing apparatus 11000.

(Steps S12010 and S12020)

In these steps, processes similar to those performed in steps S5010 and S5020 of the first embodiment are performed.

(Step S12030) Acquisition of Wide-Area Surface Profile

The wide-area surface profile acquiring unit 11030 acquires a depth image ($I_{RNG}$) of the object captured by the depth image camera 140. In this case, a still image portraying a given moment of the object is acquired as the depth image. If a position and a posture of the object are approximately the same as during measurement by the photoacoustic signal measurement apparatus 110, the still image can be acquired at any point. Alternatively, a moving image may be acquired as a depth image, in which case a frame with only a small change in the image is extracted. Next, the wide-area surface profile acquiring unit 11030 generates a wide-area surface profile (hereinafter, referred to as Surf_G) which measures a surface profile of the entire object from the depth image $I_{RNG}$ by an arbitrary known method.

(Steps S12040 and S12050)

In these steps, processes similar to those performed in steps S5040 and S5050 of the first embodiment are performed.

(Step S12060) Acquisition of Local-Area Surface Profile

The local-area surface profile extracting unit 11060 extracts a local-area surface profile of the object for each of the pulse volumes Vi ($1 \leq i \leq N\_pulse$).

In this case, a surface profile is acquired as information on a three-dimensional point group in the device coordinate system $C_{DEV}$ and stored as a local-area surface profile SurfL_i ($1 \leq i \leq N\_pulse$). Moreover, for the extraction of the local-area surface profile, known techniques that segment a body surface can be used. Alternatively, a local-area surface profile may be manually extracted. For example, a method is conceivable in which an operator specifies a position from a sectional image of a pulse volume displayed on the display apparatus 130. In this case, an interpolation process is favorably applied to the three-dimensional point group specified by the operator.

(Step S12070) Acquisition of Peak Position of Degree of Similarity Between Pulse Volumes With respect to all pairs represented by comparison pair information R_j ($1 \leq j \leq N\_pair$), the comparing unit 11070 compares pulse volumes adopted as a comparison pair with each other and acquires information regarding a degree of matching between the pair. Specifically, a degree of similarity function of the pulse volumes and a peak position of the degree of similarity function are acquired. In other words, a degree of similarity function FL_j (x, y, z) between pulse volumes to be compared when the comparison is performed while shifting a relative position of the pulse volumes by (x, y, z) is calculated as expressed by the following expression.

[Math. 13]

$$FL_j(x,y,z) = f_{simil}(I_{R_{j,1}}, I_{R_{j,2}}, x, y, z) \qquad (22)$$

where f_simil (I1, I2, x, y, z) represents a function that calculates a degree of similarity between images I1 and I2 when a relative position of the image I2 is translated by (x, y, z) with respect to the image I1. Since expression 22 simply represents one additional dimension of the amount of translation in expression 1 in step S5070 of the first embodiment, a detailed description will be omitted. In the present embodiment, each of the degree of similarity functions (FL_j: $1 \leq j \leq N\_pair$) is acquired as a three-dimensional continuous function for each piece of comparison pair information.

Next, the comparing unit 11070 calculates a position where the degree of similarity function regarding each of the comparison pairs takes a maximum value (a degree of similarity peak position). Specifically, for the degree of similarity functions (FL_j: $1 \leq j \leq N\_pair$) regarding the respective comparison pairs calculated as described above, a position PosL_j where the function value attains a maximum value is calculated as expressed by the following expression.

[Math. 14]

$$PosL_j = (PosL_{j,x}, PosL_{j,y}, PosL_{j,z}) = \operatorname*{argmax}_{x,y,z}\{FL_j(x, y, z)\} \qquad (23)$$

According to the processes described above, the comparing unit 11070 calculates degree of similarity peak positions PosL_j ($1 \leq j \leq N\_pair$) regarding all pairs.

(Step S12080) Acquisition of Peak Position of Degree of Matching Between Local-Area Surface Profile and Wide-Area Surface Profile The comparing unit 11070 compares the respective pulse volumes and the depth image with each other to acquire information regarding a degree of matching between the respective pulse volumes and the depth image. Specifically, for each of the local-area surface profiles SurfL_i ($1 \leq i \leq N\_pulse$) obtained in step S12060, the comparing unit 11070 acquires a degree of matching function with the wide-area surface profile SurfG obtained in S12030 and a peak position of the degree of matching function. An objective of the present step is to compare a wide-area image and a local-area image of the object by calculating degrees of similarity between a wide-area surface profile and local-area surface profiles of the respective pulse volumes. The following degree of matching function is acquired for each of the local-area surface profiles SurfL_i corresponding to each pulse volume.

[Math. 15]

$$FG_i(x,y,z) = f_{dist}(SurfG, SurfL_i, x, y, z) \quad (24)$$

where f_dist (Surf1, Surf2, x, y, z) represents a function for calculating a degree of matching between the surface profiles Surf1 and Surf2 when performing a comparison while shifting a relative position of the surface profile Surf2 by (x, y, z) with respect to the surface profile Surf1. Since a surface profile is expressed by a point group in the present embodiment, points that are mutually nearest neighbors in the point group may be associated with each other and an average distance between associated point groups may be applied. However, a method of calculating a degree of matching is not limited thereto. For example, a method may be used in which a degree of matching is calculated by applying a mesh constituted by triangular patches or the like from a point group representing a surface profile and comparing distances between planes constituting the mesh. In the present embodiment, with respect to each of the pulse volumes, a degree of matching function (FG_i: 1≤i≤N_pulse) is acquired as a three-dimensional continuous function.

Next, for each pulse volume, the comparing unit 11070 calculates a position where the degree of matching function with respect to the depth image takes a maximum value (a degree of matching peak position). Specifically, for each of the degree of similarity functions (FG_i: 1≤i≤N_pulse) regarding each pulse volume, a position PosG_i where the function value attains a maximum value is calculated as expressed by the following expression.

[Math. 16]

$$PosG_i = (PosGX_{i,x}, PosGX_{i,y}, PosGX_{i,z}) = \underset{x,y,z}{\operatorname{argmax}}\{FG_i(x, y, z)\} \quad (25)$$

According to the processes described above, the comparing unit 11070 calculates the degree of matching peak position PosG_i (1≤i≤N_pulse) with respect to the depth image for all pulse volumes.

(Step S12090) Estimation of Body Motion for Each Pulse Based on Two Types of Peak Positions The comparing unit 11070 obtains a pulse position estimation amount Pos_i (1≤i≤N_pulse) from the degree of similarity peak position PosL_j (1≤j≤N_pair) obtained in step S12070 and the degree of matching peak position PosG_i (1≤i≤N_pulse) obtained in step S12080. In other words, positions of all pulse volumes are comprehensively optimized while maintaining, to the greatest extent possible, an individual optimum value regarding relative positions between local-area images (pulse volumes) of the object and an individual optimum value regarding a position of each local-area image with respect to a wide-area image (a depth image) of the object. This process is similar to that of step S5090 according to the first embodiment. For the present step, a degree of similarity peak position between projection images in step S5090 is replaced with a degree of similarity peak position between pulse volumes and a degree of similarity peak position of a projection image with respect to an infrared camera image is replaced with a degree of matching peak position of a local-area surface profile with respect to a wide-area surface profile.

(Steps S12100 and S12110)

In these steps, processes similar to those performed in steps S5100 and S5110 of the first embodiment are performed.

As described above, with the image processing apparatus according to the present embodiment, a photoacoustic image can be corrected based on a comparison of only information in a three-dimensional space by acquiring a three-dimensional surface profile of an object from a depth image of the object. Accordingly, a motion of the object can be corrected without any loss of information to be compared which occurs when degrading the information to a lower-dimensional space.

(Modification 3-1) Wide-Area Surface Profile May be Acquired from Ultrasonic Image In the third embodiment described above, as the process of step S11030, a wide-area surface profile of an object is extracted from a depth image. However, a method of acquiring a wide-area surface profile is not limited thereto. For example, a wide-area surface profile may be extracted from an ultrasonic image obtained by performing an ultrasonic measurement of the object. In this case, the wide-area surface profile acquiring unit 11030 acquires an ultrasonic volume of the entire object using an ultrasonic imaging apparatus (not shown) and extracts a wide-area surface profile. In doing so, for example, a wide-area surface profile of the object can be acquired by extracting a boundary attributable to a difference in acoustic impedances between inside and outside of the object by threshold processing. Accordingly, for example, when the object is immersed in water, although imaging conditions for a depth image camera are poor, a significant difference in acoustic impedances between water and the object (such as a human body) enables a wide-area surface profile to be acquired with high precision.

(Modification 3-2) Degree of Matching of Local-Area Surface Profiles May be Calculated when Comparing Pulse Volumes In the third embodiment described above, as the process performed in step S12070, a degree of image similarity between pulse volumes is considered a degree of matching and a peak position thereof is calculated. However, a degree of matching between pulse volumes may be calculated using any other methods. For example, an anatomical characteristic such as a blood vessel branch may be extracted from each pulse volume by image processing and a degree of matching between positions or distributions of the anatomical characteristic may be used as the degree of matching between the pulse volumes. Alternatively, a degree of matching of local-area surface profiles between pulse volumes may be calculated and used as the degree of matching between the pulse volumes. Since the degree of matching can be calculated by adopting local-area surface profiles of two different pulse volumes instead of a wide-area surface profile in the process of calculating a degree of matching function between a wide-area surface profile and a local-area surface profile in step S12080, a description thereof will be omitted. Accordingly, since only a comparison with respect to a limited region in a three-dimensional space is required as compared to a calculation of a degree of image similarity which requires comparisons in units of voxels which are spread throughout the three-dimensional space, calculation cost can be reduced.

Fourth Embodiment

An image processing apparatus according to a fourth embodiment uses a camera image that only portrays an external appearance of an object instead of an infrared camera image as a wide-area image of the object. The following description will focus on differences from the respective embodiments described above.

(Apparatus Configuration)

Figure 13:
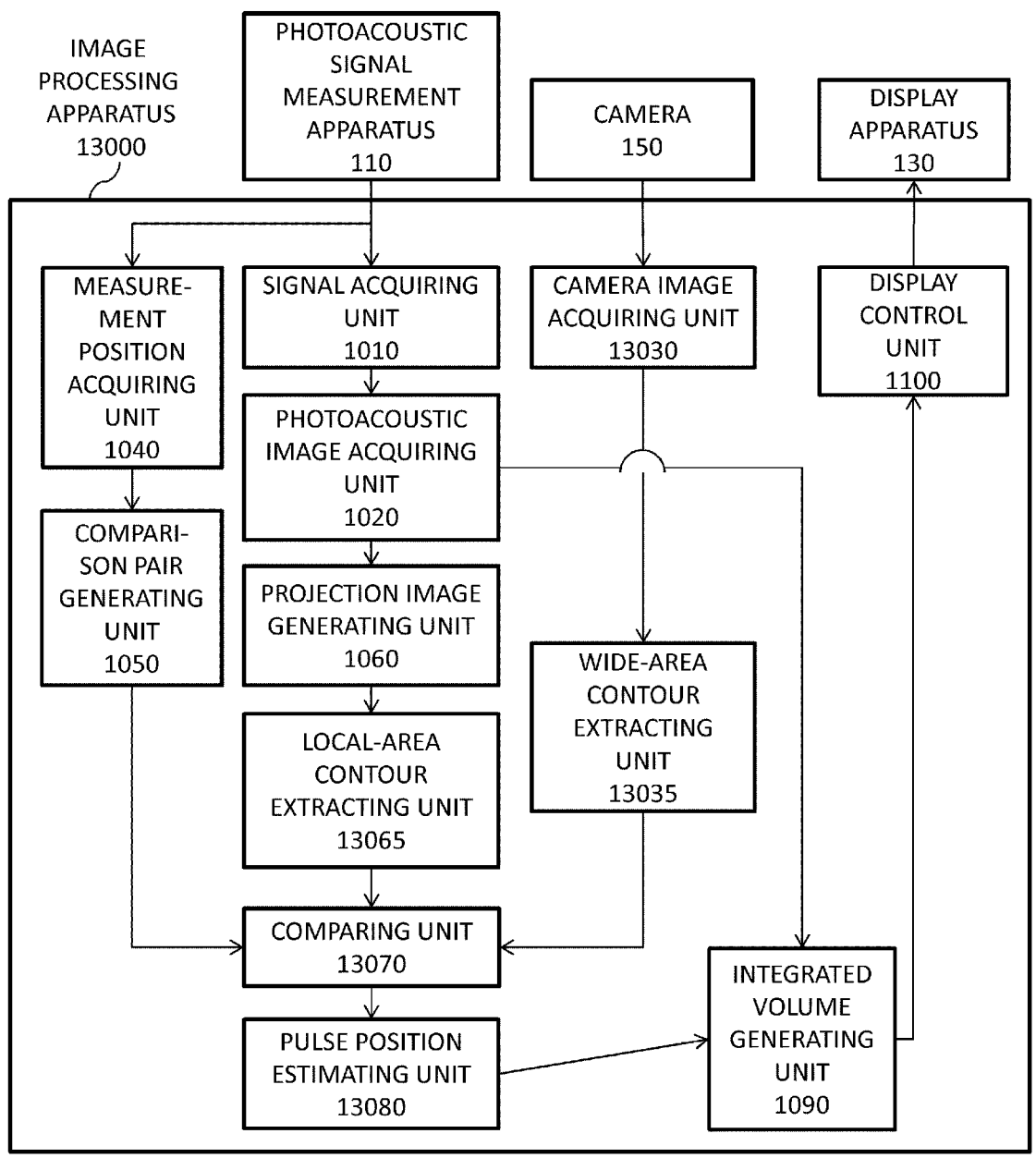
FIG. 13 is a diagram showing a functional configuration of an image processing apparatus according to a fourth embodiment.

Hereafter, a configuration of a photoacoustic apparatus according to the present embodiment will be described with reference to FIG. 13. It should be noted that components similar to those of the embodiments described above will be denoted by the same reference numerals and a description thereof will be omitted.

A camera 150 is a camera that photographs an external appearance of an object (light in the visible range) and is installed at a position that enables the external appearance of the entire object to be photographed. Unlike the infrared camera 120 according to the first embodiment, the camera 150 photographs color images. Otherwise, the description of the infrared camera 120 in the first embodiment may be considered to apply to the camera 150 by replacing the term "infrared camera" with the term "camera".

An image processing apparatus 13000 includes a signal acquiring unit 1010, a photoacoustic image acquiring unit 1020, a camera image acquiring unit 13030, a measurement position acquiring unit 1040, a comparison pair generating unit 1050, a projection image generating unit 1060, and a local-area contour extracting unit 13065. The apparatus further includes a comparing unit 13070, a pulse position estimating unit 13080, an integrated volume generating unit 1090, and a display control unit 1100.

The camera image acquiring unit 13030 acquires a camera image (two-dimensional image) captured by the camera 150 as a wide-area image and outputs the wide-area image to a wide-area contour extracting unit 13035.

The wide-area contour extracting unit 13035 extracts a two-dimensional contour of a wide area of the object from the camera image and outputs the extracted contour (hereinafter, referred to as a wide-area contour) to the comparing unit 13070.

The local-area contour extracting unit 13065 extracts a local two-dimensional contour of the object from a projection image of a local area of the object and outputs the extracted contour (hereinafter, referred to as a local-area contour) to the comparing unit 13070.

Based on comparison pair information, the comparing unit 13070 performs a process similar to that performed by the comparing unit 1070 according to the first embodiment as a process of comparing pulse volumes forming the pair (first comparison). In addition, the comparing unit 13070 performs a process of comparing each pulse volume and the camera image with each other (second comparison). Specifically, the comparing unit 13070 compares the local-area contour acquired from the local-area contour extracting unit 13065 and the wide-area contour acquired from the wide-area contour extracting unit 13035 with each other, calculates information regarding a degree of matching between the local-area contour and the wide-area contour, and outputs the information to the pulse position estimating unit 13080.

The pulse position estimating unit 13080 calculates estimation values of positions of the respective pulse volumes (pulse position estimation amounts) based on both the information regarding the degree of matching between the pair and the information regarding the degree of matching between the respective pulse volumes and the camera image as calculated by the comparing unit. The calculated estimation values are output to the integrated volume generating unit 1090.

(Processing Flow)

Figure 14:
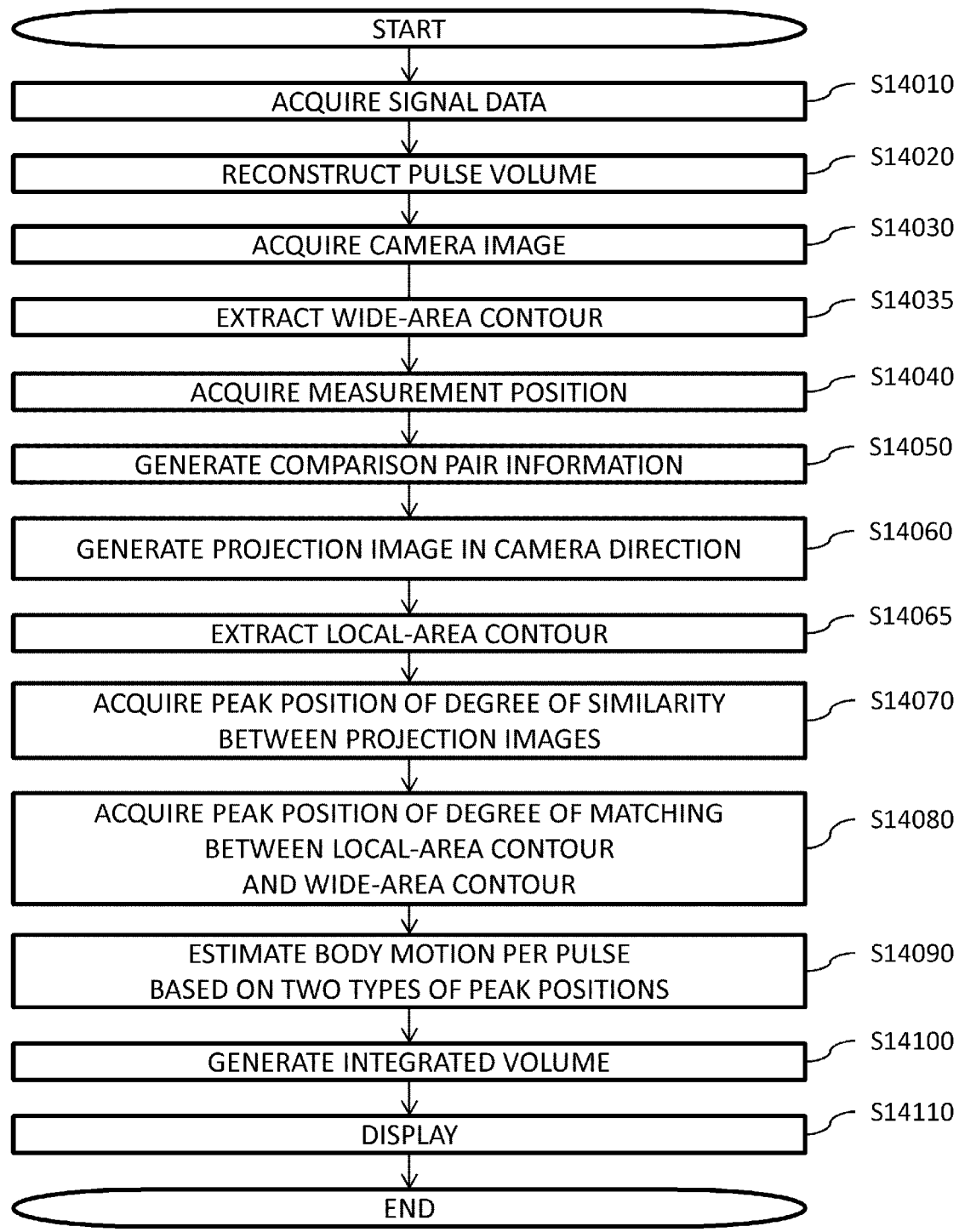
FIG. 14 is a flow chart showing an overall processing procedure according to the fourth embodiment.

FIG. 14 is a flow chart showing an overall procedure of processing performed by the image processing apparatus 13000.

(Steps S14010 and S14020)

In these steps, processes similar to those performed in steps S5010 and S5020 of the first embodiment are executed.

(Step S14030)

The camera image acquiring unit 13030 acquires camera images ($I_{CAM1}$, $I_{CAM2}$, and $I_{CAM3}$) of the object photographed by the cameras 301, 302, and 303. This process is comparable to replacing "infrared camera" with "camera" in step S5030 according to the first embodiment.

(Step S14035) Extraction of Wide-Area Contour

The wide-area contour extracting unit 13035 extracts a contour of the object from each of the camera images ($I_{CAM1}$, $I_{CAM2}$, and $I_{CAM3}$). For example, a general edge detection method can be used to extract the contours. The extracted wide-area contours will be respectively defined as Surf_G1, Surf_G2, and Surf_G3.

(Steps S14040 and S14050)

In these steps, processes similar to those performed in steps S5040 and S5050 of the first embodiment are performed.

(Step S14065) Extraction of Local-Area Contour

The local-area contour extracting unit 13065 extracts a local-area contour of the object from each projection image. Since the projection image is a projection image of a pulse volume, portrayed structural information is no different from a pulse volume. Therefore, the present step can be executed in a similar manner to performing the process of step S12060 of the third embodiment in a two-dimensional region. The extracted local-area contours are respectively denoted as SurfLx_i, SurfLy_i, and SurfLz_i ($1 \le i \le N\_pulse$).

(Step S14070)

In the present step, a process similar to that performed in step S5070 of the first embodiment is performed.

(Step S14080) Acquisition of Peak Position of Degree of Matching Between Local-Area Contour and Wide-Area Contour The comparing unit 13070 compares the respective pulse volumes and the camera image with each other to acquire information regarding a degree of matching between the respective pulse volumes and the camera image.

Specifically, degree of contour matching functions between the respective local-area contours SurfLx_i, SurfLy_i, and SurfLz_i and corresponding wide-area contours Surf_G2, Surf_G3, and Surf_G1 extracted in step S14035 are acquired. In addition, peak positions of the acquired degree of matching function are acquired. An objective of the present step is to compare a wide-area image and a local-area image of the object with each other by calculating degrees of similarity of local-area contours of the respective pulse volumes with respect to the wide-area contour generated from the camera image.

When acquiring the degree of matching functions, functions FGx_i, FGy_i, and FGz_i are acquired for a local-area contour in each direction in a similar manner to expression 24 in step S12080 of the third embodiment. The only difference is that, while expression 24 causes a local-area surface profile to be translated on three-dimensional coordinates, a local-area contour is translated on two-dimensional coordinates in the present embodiment. Specific two-dimensional coordinates are: (y, z) for FGx_i; (z, x) for FGy_i; and (x, y) for FGz_i. In addition, when calculating a peak position PosG_i ($1 \le i$ N_pulse) of the degree of matching functions, the degree of similarity functions FGX_i, FGY_i, and FGZ_i in the respective axial directions in step S5080 of the first embodiment may be replaced with the degree of matching functions.

(Step S14090) Estimation of Body Motion for Each Pulse Based on Two Types of Peak Positions The comparing unit 13070 calculates a pulse position estimation amount Pos_i ($1 \leq i \leq N\_pulse$) from the degree of similarity peak position PosL_j ($1 \leq j \leq N\_pair$) obtained in step S14070 and the degree of matching peak position PosG_i ($1 \leq i \leq N\_pulse$) obtained in step S14080. In other words, comprehensive optimization of all pulse volumes is performed while maintaining, to the greatest extent possible, an individual optimum value regarding relative positions between local-area images (projection images) of the object and an individual optimum value regarding a position of each local-area image with respect to a wide-area image (a camera image) of the object. Accordingly, the pulse position estimation amount Pos_i ($1 \leq i \leq N\_pulse$) is calculated. The process of the present step replaces the degree of similarity peak position of a projection image with respect to an infrared camera image in step S5090 of the first embodiment with a degree of matching peak position of a local-area contour with respect to a wide-area contour.

As described above, according to the present embodiment, a photoacoustic image can be corrected by acquiring a contour of an object from a camera image of the object and comparing the contour with a profile extracted from the photoacoustic image. Accordingly, a motion of an object can be corrected using a general-purpose camera which offers advantages in terms of availability and cost.

OTHER EMBODIMENTS

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™) a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-080675, filed on Apr. 10, 2015, which is hereby incorporated by reference herein in its entirety.

What is claimed is:

1. A photoacoustic apparatus comprising:
   a light source;
   a receiving element configured to receive an acoustic wave generated from an object irradiated with light from the light source;
   a processor configured to generate image data representing characteristics information regarding the inside of the object using the acoustic wave;
   a changer configured to change irradiation positions of the light on the object; and
   a wide-area image acquirer configured to acquire a wide-area image of the object, wherein
   the processor is configured to
   generate, for the irradiation positions that are changed by the changer, a local-area image that is the image data in a local area of the object corresponding to the irradiation position, and
   based on a first comparison that is a comparison between a plurality of local-area images obtained for the irradiation positions and a second comparison that is a comparison between the plurality of local-area images and the wide-area image, integrate the plurality of local-area images.

2. The photoacoustic apparatus according to claim 1, wherein
   the processor is configured to generate, for the local areas, volume data as the local-area image using the acoustic wave.

3. The photoacoustic apparatus according to claim 2, wherein
   the processor is configured to perform the first comparison by generating projection images of the local-area images and acquiring information regarding a degree of matching between the projection images.

4. The photoacoustic apparatus according to claim 1, wherein
   the processor is configured to regard the local-area images having portions that overlap with each other as a pair, and compares, as the first comparison, the local-area images forming the pair with each other.

5. The photoacoustic apparatus according to claim 1, wherein
   the processor is configured to perform the second comparison by acquiring information regarding a degree of matching between the wide-area image and the local-area image.

6. The photoacoustic apparatus according to claim 1, wherein
   the processor is configured to perform the integration by using information regarding a degree of matching between the plurality of local-area images on the basis of the first comparison and information regarding a degree of matching between the plurality of the local-area images and the wide-area image on the basis of the second comparison.

7. The photoacoustic apparatus according to claim 1, wherein
   the processor is configured to perform integration of the plurality of local-area images on the basis of the first comparison, and subsequently deforms the integrated image on the basis of the second comparison.

8. The photoacoustic apparatus according to claim 1, wherein
   the wide-area image acquirer is an infrared camera which acquires an infrared image of the object.

9. The photoacoustic apparatus according to claim 1, wherein
the wide-area image acquirer is configured to acquire a three-dimensional surface profile based on a depth image of the object as the wide-area image.

10. The photoacoustic apparatus according to claim 1, wherein
the wide-area image acquirer is a camera which acquires an image portraying an external appearance of the object.

11. The photoacoustic apparatus according to claim 2, wherein
the processor is configured to perform the second comparison by generating respective projection images of the plurality of local-area images and acquiring information regarding a degree of matching between the projection images and the wide-area image.

12. The photoacoustic apparatus according to claim 11, wherein
the wide-area image acquirer is a camera, and
the processor is configured to generate the projection image by projecting the local-area image in approximately the same direction as an imaging direction of the camera.

13. The photoacoustic apparatus according to claim 1, wherein
the processor is configured to correct a positional displacement of the plurality of local-area images caused by a body motion of the object while an acoustic wave for generating the plurality of local-area images is being acquired based on results of the first comparison and the second comparison when integrating the plurality of local-area images.

14. An image processing method for generating image data representing characteristics information regarding the inside of an object irradiated with light while changing irradiation positions using an acoustic wave generated from the object, the image processing method comprising:
acquiring a wide-area image of the object;
generating, for the changing irradiation positions, a local-area image that is the image data in a local area of the object corresponding to the irradiation position; and
based on a comparison between a plurality of the local-area images obtained for the irradiation positions and a comparison between the plurality of local-area images and the wide-area image, integrating the plurality of local-area images.

* * * * *